US008192854B2

(12) United States Patent
Borole

(10) Patent No.: US 8,192,854 B2
(45) Date of Patent: Jun. 5, 2012

(54) MICROBIAL FUEL CELL TREATMENT OF ETHANOL FERMENTATION PROCESS WATER

(75) Inventor: Abhijeet P. Borole, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 791 days.

(21) Appl. No.: 12/366,713

(22) Filed: Feb. 6, 2009

(65) Prior Publication Data
US 2010/0203359 A1 Aug. 12, 2010

(51) Int. Cl.
H01M 8/16 (2006.01)
C12P 7/08 (2006.01)
C12P 7/10 (2006.01)
C12P 7/12 (2006.01)
H01M 9/00 (2006.01)

(52) U.S. Cl. ............ 429/2; 429/401; 435/163; 435/164; 435/165

(58) Field of Classification Search ............... None
See application file for complete search history.

(56) References Cited

U.S. PATENT DOCUMENTS

| 4,384,897 | A | 5/1983 | Brink |
| 5,620,877 | A | 4/1997 | Farone et al. |
| 6,251,643 | B1 | 6/2001 | Hansen et al. |
| 6,555,350 | B2 | 4/2003 | Ahring et al. |
| 6,927,048 | B2 | 8/2005 | Verser et al. |
| 7,351,559 | B2 | 4/2008 | Verser et al. |
| 2002/0192774 | A1 | 12/2002 | Ahring et al. |
| 2007/0141691 | A1 | 6/2007 | Hirl |
| 2007/0184541 | A1 | 8/2007 | Karl et al. |
| 2007/0190626 | A1 | 8/2007 | Wilkening et al. |
| 2007/0259217 | A1 | 11/2007 | Logan |
| 2007/0270511 | A1 | 11/2007 | Melnichuk et al. |
| 2007/0275447 | A1 | 11/2007 | Lewis et al. |
| 2008/0003654 | A1 | 1/2008 | Hirl |
| 2008/0277272 | A1 | 11/2008 | Pierce et al. |
| 2008/0277273 | A1 | 11/2008 | Logan |
| 2009/0017512 | A1* | 1/2009 | May et al. ............... 435/165 |
| 2009/0297890 | A1* | 12/2009 | Shimomura et al. ....... 429/2 |
| 2010/0178530 | A1* | 7/2010 | Min et al. ................. 429/2 |

OTHER PUBLICATIONS

Lovley D. R., "Bug juice: Harvesting Electricity with Microorganisms" *Nature Reviews Microbiology* 4:497-508 (2006).
Mosier N. et al., "Features of Promising Technologies for Pretreatment of Lignocellulosic Biomass" *Bioresource Technology* 96:673-686 (2005).
Schell D., "Biochemical Processing Integration Biochemical Platform Review Meeting" (Aug. 7-9, 2007).

* cited by examiner

*Primary Examiner* — Krishnan S Menon
(74) *Attorney, Agent, or Firm* — Scully, Scott, Murphy & Presser, P.C.

(57) ABSTRACT

The present invention relates to a method for removing inhibitor compounds from a cellulosic biomass-to-ethanol process which includes a pretreatment step of raw cellulosic biomass material and the production of fermentation process water after production and removal of ethanol from a fermentation step, the method comprising contacting said fermentation process water with an anode of a microbial fuel cell, said anode containing microbes thereon which oxidatively degrade one or more of said inhibitor compounds while producing electrical energy or hydrogen from said oxidative degradation, and wherein said anode is in electrical communication with a cathode, and a porous material (such as a porous or cation-permeable membrane) separates said anode and cathode.

36 Claims, 10 Drawing Sheets

MICROBIAL FUEL CELL TREATMENT OF ETHANOL FERMENTATION PROCESS WATER

This invention was made with government support under Contract Number DE-AC05-00OR22725 between the United States Department of Energy and UT-Battelle, LLC. The U.S. Goverment has certain rights in this invention.

FIELD OF THE INVENTION

The present invention relates generally to the treatment of process waters by microbial fuel cells, and particularly, as applied to the ethanol fermentation process.

BACKGROUND OF THE INVENTION

Cellulosic ethanol refers to ethanol that has been produced from the cellulosic components of plants (i.e., cellulosic biomass) as opposed to ethanol produced from starches and sugars (e.g., corn ethanol). Cellulosic ethanol is increasingly being viewed as a preferred fuel alternative to starch or sugar ethanol because cellulosic parts of plants (e.g., corn stover) are generally non-edible and undesirable byproducts resulting from harvesting of edible crops, and thus, do not compete with food production. Typically, the cellulosic remnants are either discarded, used as fertilizer, or used as fodder. Furthermore, since cellulosic byproducts are not specifically produced as a fuel source, they do not require any additional expenditure for their production, and are therefore cheap and plentiful.

In a typical cellulosic ethanol process, raw cellulosic biomass material is pretreated in order to convert, or partially convert, cellulosic and hemicellulosic components into enzymatically hydrolyzable components (e.g., poly- and oligo-saccharides). The pretreatment process also serves to separate the cellulosic and hemicellulosic components from solid lignin components also present in the raw cellulosic material. The pretreatment process typically involves reacting the raw cellulosic biomass material, typically as a finely divided mixture or slurry in water, with an acid, such as sulfuric acid. Other common pretreatment processes include, for example, hot water treatment, wet oxidation, steam explosion, elevated temperature (e.g., boiling), alkali treatment and/or ammonia fiber explosion (see Mosier et. al., *Bioresource Technology*, 96 (2005) 673-686).

Typically, the pretreated biomass is then treated by a saccharification step in which poly- and oligo-saccharides are enzymatically hydrolyzed into simple sugars. The free sugars and/or oligosaccharides produced in the saccharification step are then subjected to fermentation conditions for the production of ethanol. Typically, fermentation is accomplished by combining one or more fermenting microorganisms with the produced sugars under conditions suitable for fermentation. The fermenting broth is typically heated, e.g., to 20-40° C. for yeast organisms (such as *Saccharomyces cerevisiae*), or to higher temperatures for thermophilic organisms (such as *Thermoanaerobacter* species). The ethanol is then removed (or partially removed) from the broth (e.g., by distillation), thereby leaving behind fermentation process water.

A significant problem encountered in the biomass-to-ethanol production process is the production of inhibitory compounds (e.g., acetate, furfural (and other aromatic aldehydes), ketones, and alcohols, such as hydroxy aromatics) during the pretreatment process of the raw cellulosic material. Inhibitor compounds have the deleterious effect of inhibiting one or more process steps (e.g., the saccharification or fermentation processes), thereby causing a decreased level of ethanol production. In particular, acetate is generally produced from hydrolysis of acetylated ferulates which are associated with the hemicellulose fraction of biomass.

Since copious amounts of water are used in the processing of cellulosic biomass materials, it is highly desirable to recycle used process water that has been separated from ethanol at the end of the fermentation process. However, since the process water contains inhibitory compounds, recycling process water to an earlier step has the effect of causing an accumulation (i.e., increasing concentration) of inhibitory compounds used in the process. Eventually, the concentration of inhibitory compounds can be high enough to reduce efficiency of the process to a level that renders the process unfeasible (e.g., at or below 10% yields of ethanol).

The accumulation of inhibitor compounds is compounded and accelerated by the general practice of using a high solids loading (i.e., generally at least 20% solids loading) of raw biomass in the process. Both recycling and high solids loading can dramatically lower ethanol yields. For example, for a high solids loading of 25%, an increase in water recycling from 10% to 25% can result in a reduction in ethanol yield from 65% to 5% (Schell, *DOE OBP Biochemical Processing Integration, Biochemical Platform Review Meeting*, Denver, Colo., Aug. 7-9, 2007).

The accumulation of inhibitory compounds caused by recycling discourages recycling and conservation of process water, and encourages disposal of contaminated water (often into the environment) and replacement with fresh water. If water recycling is pursued, the methods for removing inhibitors are generally costly and environmentally unfriendly by requiring the use of non-renewable fuels. Some examples of currently practiced inhibitor-removal processes include, for example, separation methods (e.g., by use of specialty membranes or ion exchange membranes), and anaerobic digestion or microbial gasification (e.g., methanation).

Accordingly, there would be a benefit in a cost efficient method that removes inhibitor compounds from process water used in a cellulosic biomass-to-ethanol process. There would be a particular benefit in such a method in which significant cost savings results from use of renewable energy technology. Such a method would beneficially promote conservation of water by allowing ethanol fermentation wastewater to be recycled, while at the same time maintaining high ethanol yields in a continuously recycled system. In addition, such a method would allow a portion of the process water that is not recycled to be safely discharged into the environment.

SUMMARY OF THE INVENTION

The present invention provides a method for removing inhibitor compounds (i.e., "inhibitors") from process water used in a cellulosic biomass-to-ethanol process (hereinafter also referred to as a "cellulosic ethanol process") wherein one or more microbial fuel cells (MFCs) consume the inhibitor compounds and advantageously produce electrical energy therefrom. The electrical energy can advantageously be used to power any desired process, and more preferably, one or more processes in the cellulosic biomass-to-ethanol process. The invention is also directed to a MFC (or system of MFCs) for practicing the method. In addition, the invention is directed to methods of operating the MFC for optimal performance.

In a preferred embodiment, the method is directed to removing inhibitor compounds from a cellulosic biomass-to-ethanol process which includes an initial pretreatment step of raw cellulosic biomass material. The inhibitory compounds generally include sugar degradation products (e.g., furfural and 5-hydroxymethylfurfural), lignin degradation products (e.g., aromatic aldehydes, ketones, alcohols or acids) and other organic acids such as acetate resulting from hemicellulose hydrolysis or biomass fermentation. In a particular embodiment, the inhibitory compounds include at least one or more of acetate, furfural, and one or more hydroxy aromatics. The method includes treating fermentation process water (hereinafter also referred to as "process water"), from which ethanol has been removed, with one or more microbial fuel cells that oxidatively degrade inhibitor compounds present in the process water. The microbial fuel cell operates by reacting inhibitor compounds with microbes in contact with an anode of the microbial fuel cell. The microbes are capable of oxidatively degrading (i.e., consuming) the inhibitor compounds and transferring produced electrons to the anode during the course of the degradation process. The inhibitor compounds are removed from the process water such that their individual or total concentration is below an inhibitory concentration capable of interfering with any one or more process steps in the cellulosic biomass-to-ethanol process. The anode is in electrical communication with a cathode of the microbial fuel cell. A porous material, such as a cation-permeable material, typically separates the anode and cathode.

In another embodiment, the MFC is operated in such a manner that hydrogen is produced at the cathode during microbial consumption of inhibitor compounds or materials. The hydrogen gas can be used for any useful purpose, such as a commodity chemical, a reactant in the cellulosic biomass-to-ethanol process, or as a fuel source to power one or more processes in the cellulosic biomass-to-ethanol process.

In another embodiment, the MFC is operated in such a manner that the cathode electrochemically reduces one or more electrochemically reducible species, such as a nitrate, chlorate, peroxide, or reducible metal species, during microbial consumption of inhibitor compounds or materials at the anode.

Thus, as will be described in further detail below, the method advances and improves the production of ethanol, a promising environmentally-friendly fuel, from cheap and renewable cellulosic feedstock. In particular, the method advantageously provides an economical, convenient, and environmentally friendly method for removing inhibitor compounds from a cellulosic biomass-to-ethanol process. Significantly, by implementation of the method and fuel cell system described herein, process water can be partly or wholly recycled without inhibiting the ethanol production process.

DETAILED DESCRIPTION OF THE INVENTION

Figure 1:
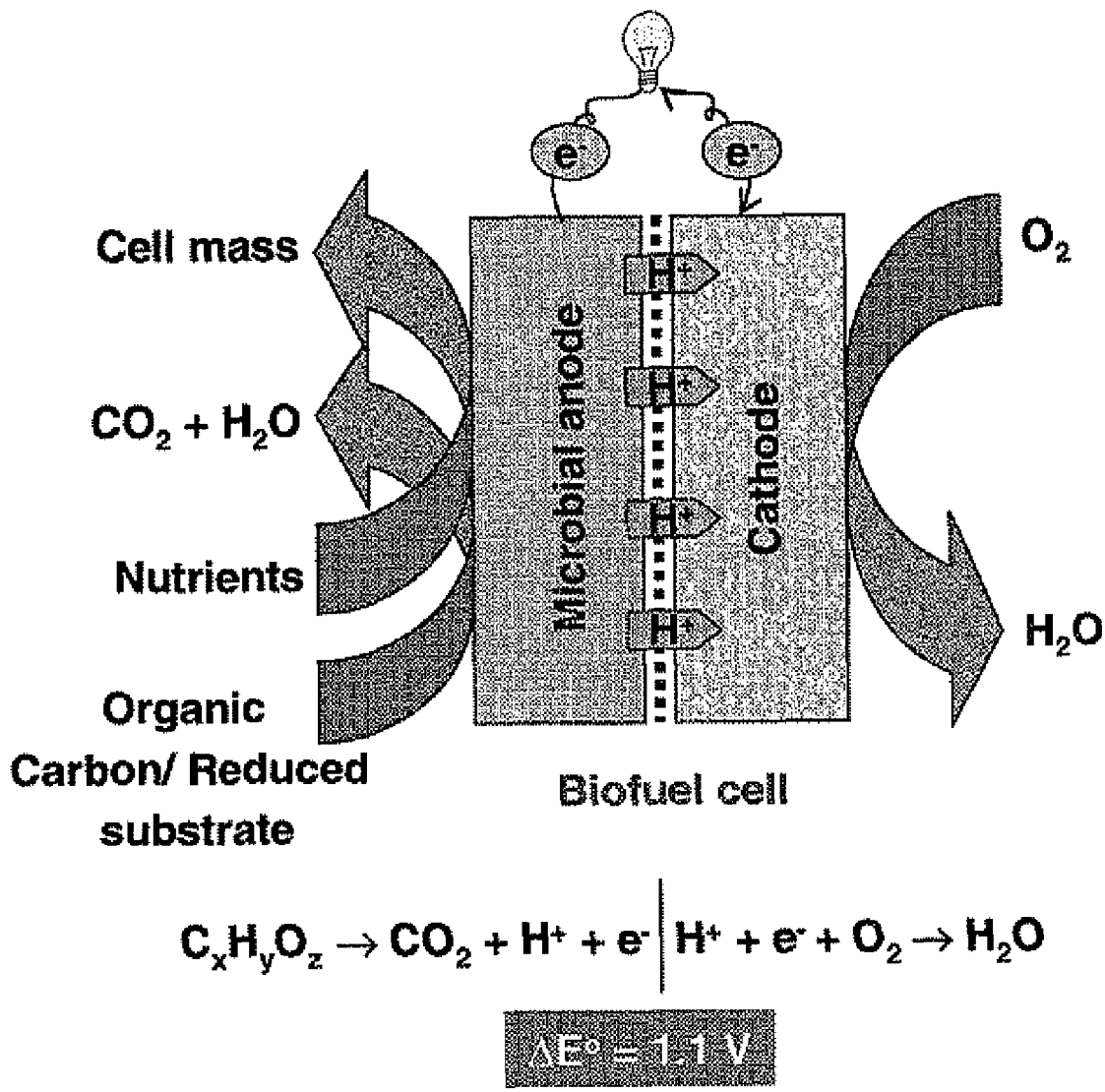
FIG. 1. Depiction of a preferred MFC design for the present invention.

In one aspect, the invention is directed to a method for removing inhibitor compounds from process water used in a cellulosic ethanol process. In the method, process water containing one or more inhibitors is processed by a microbial fuel cell as further described below. As used herein, "microbial fuel cell" also includes a system of microbial fuel cells (i.e., two or more MFCs used in the process). Any cellulosic ethanol process that employs a pretreatment process known to produce inhibitor compounds can benefit by the method described herein.

In one embodiment, the cellulosic ethanol process is conducted such that the process water contains inhibitor chemicals in the substantial absence of non-inhibitory nutrient compounds or materials (e.g., sugars, oligosaccharides, and ethanol). For example, the fermentation process can be made to be essentially complete, i.e., converting substantially all simple sugars into ethanol such that there is a substantial absence of non-inhibitory nutrients in the process water.

In another embodiment, the cellulosic ethanol process is conducted such that the process water contains inhibitor chemicals along with residual concentrations of undigested materials in order to provide the microbes of the MFC with additional nutritive material from which additional electrical energy can be produced. The residual concentration of nutrient materials in the fermentation process water can be, for example, 0.5%, 1%, 2%, 5%, or 10% by weight of the process water, or amounts greater or less than these values, or any range resulting from any two of these values.

The raw cellulosic biomass considered herein can be any cellulose-containing or lignocellulose-containing material which can be used in a fermentative ethanol production process and which tends to form inhibitor compounds upon pretreatment. Particularly considered herein as a cellulosic biomass material is corn stover, which generally includes at least one of the leaves, husks, stalks, or cobs of corn plants. Other suitable cellulosic biomass material includes, for example, switchgrass (i.e., *Panicum virgatum*), miscanthus, sugarcane, woodchips, saw dust, paper pulp, and hemp.

The inhibitor compounds (i.e., "inhibitors") include any compound or material that can function to partly, substantially, or completely inhibit (i.e., generally "interfere with") one or more process steps in the cellulosic ethanol process. Some of the process steps that can be inhibited by such compounds include, for example, the saccharification step or fermentation step. The inhibitors are commonly either sugar degradation products (e.g., furfural and 5-hydroxymethylfurfural) and/or lignin degradation products (e.g., aromatic aldehydes, ketones, alcohols, and acids). The inhibitors can include, for example, one or more aliphatic carboxylic acids, aliphatic ketones, aliphatic aldehydes, aliphatic alcohols, aromatic carboxylic acids, aromatic ketones, aromatic aldehydes, and/or aromatic alcohols, wherein the aliphatic inhibitors typically contain from 1, 2, or 3 and up to 8, 9, or 10 carbon atoms, and the aromatic inhibitors typically contain from 5, 6, or 7 and up to 12, 13, or 14 carbon atoms. Often, the inhibitors include at least one or more compounds selected from carboxylic acids (i.e., carboxylates), furfural (i.e., 2-furfural), 5-hydroxymethylfurfural, and phenolic compounds. The carboxylic acid can be, for example, acetic acid (acetate), propanoic acid, or higher acids, or their deprotonated (e.g., salt) forms. The phenolics are typically those resulting from lignin degradation. The phenolics can be, for example, phenol, guaiacol, eugenol, cresols, syringol, 4-hydroxybenzaldehyde (4-HB or HB), vanillin, vanillic acid (VA), homovanillic acid, syringaldehyde, 3,4,5-trimethoxybenzaldehyde, 4-hydroxyacetophenone (4-HAP or HAP), acetovanillone, acetosyringone, 4-hydroxybenzoic acid, syringic acid, 3,4,5-trimethoxyacetophenone, ferulic acid, caffeic acid, sinapyl alcohol, coniferyl alcohol, and p-coumaric acid.

Derivative compounds of inhibitors may also be present in the process water. In one embodiment, the one or more derivative compounds also function as inhibitor compounds. In another embodiment, the derivative compounds do not function as inhibitor compounds. Some derivatives of carboxylic acid inhibitor compounds include the dicarboxylic acids (e.g., maleic, fumaric, and glutaric acid), the anhydrides, and organoesters. Some derivatives of hydroxy aromatic inhibitor compounds include their dimers, oligomers, polymers, and ethers. Some derivatives of furfural include furfuryl alcohol, furoic acid, and 5-hydroxymethylfurfural (5-HMF or HMF).

By "removing" or "cleansing" fermentation process waters of one or more inhibitor compounds is meant that the concentration (i.e., level) of one or more of the inhibitor compounds is reduced to a level below an inhibitory concentration capable of interfering with one or more process steps of the cellulosic ethanol process. In other words, the concentration of one or more inhibitor compounds is reduced to a subinhibitory concentration.

Preferably, the process water is cleansed such that the process water experiences at least a 20% reduction in one or more inhibitor substances. More preferably, the process water is cleansed such that the process water experiences at least a 30%, or 40%, or 50%, or 60%, or 70%, or 80%, or 90%, or 95%, or 97%, or 98%, or 99% reduction in one or more (or total of) inhibitors. Even more preferably, the process water is cleansed such that one or more inhibitors have been substantially removed from the wastewater, i.e., greater than 95% reduction in inhibitor concentration (more preferably, at least 98% or 99% reduction in inhibitor concentration).

The concentration of one or more inhibitors in the raw (i.e., MFC-untreated) process water can typically be, for example, at or greater than (or at or less than) 1 mM, 2 mM, 5 mM, 10 mM, 15 mM, 20 mM, 30 mM, 40 mM, or 50 mM, or within a range governed by any two of these values. The level of acetate in raw process water can be significantly higher than these values, e.g., up to 100 mM, 200 mM, 300 mM, 400 mM, or 500 mM. Any of the foregoing concentrations can also represent an inhibitory concentration, i.e., a concentration of one or more inhibitors at and/or above which a process step is partly or completely inhibited. Depending on the potency of the inhibitor, the MFC can be used to treat the process water such that the concentration of one or more (or total of) inhibitors is no more than, for example, any of the exemplary concentrations of inhibitors given above. The MFC may also be used to treat the process water such that the concentration of one or more (or total of) inhibitors is essentially negligible for the process, e.g., at or less than 1 mM, 0.5 mM, or 0.1 mM.

The cleansed process water can be used for any desired purpose or discharged into the environment, if appropriate. In a preferred embodiment, at least a portion of the cleansed process water is recycled into the cellulosic ethanol process. More preferably, the process water is continuously recycled. By being "continuously recycled" is meant that at least a portion of cleansed process water resulting from one process cycle is recycled into a next (or subsequent) process cycle wherein fresh raw biomass is to be processed using the recycled water. The recycling can be continued for any number of process cycles as found suitable. Preferably, at least 10%, more preferably at least 15%, more preferably at least 20%, and more preferably at least 25% of the cleansed process water is continuously recycled. In particular embodiments, at least 30%, or 40%, or 50%, or 60%, or 70%, or 80%, or 90%, or 95% of the cleansed process water is continuously recycled.

The process can be operated using any suitable solids loading value, which refers to the amount of raw biomass being processed at the start of the process relative to the total weight of the raw biomass and process water. The solids loading is also referred to herein as the "biomass loading". Some biomass loading values include, for example, 20%, 25%, 30%, 35%, and 40%, as well as values greater than or below these values, or a range resulting from any two of these values.

In a preferred embodiment, the invention is practiced by continuous recycling at any solids loading value (preferably, with at least 20% solids loading or higher) while maintaining at least a 50% ethanol yield per process cycle. More preferably, continuous recycling is employed using a solids loading value at or above 20% while maintaining at least a 60%, 70%, 80%, 90%, or 95% ethanol yield per process cycle, or a range governed by any two of the foregoing ethanol yield values (e.g., 50-90% or 60-90% ethanol yields).

In a particular embodiment, the cleansing process is conducted such that the concentration (and more preferably, loading rate) of inhibitors and any other consumables in the process water entering the MFC is at or below a concentration or loading rate at which the MFC can operate at a maximum electrical power output (i.e., capacity) and coulombic efficiency. The concentration or loading rate of total consumables can be desirably adjusted to, for example, 90% or less or 80% or less of a concentration or loading rate at which the MFC can operate at a maximum electrical output capacity. The foregoing embodiment may be preferred in a situation where the MFC has the potential to produce methane from the consumables (e.g., as would be expected from methanogenic bacteria). If the microbes being used are capable of producing methane from the consumables, the likelihood of producing methane is increased when an excess of consumables (i.e., an amount of the consumables above a concentration at which the MFC can operate at maximum electrical power output) is used. Since production of methane in the MFC is undesired according to the present invention, the foregoing modification can be advantageous in this respect.

As used herein, and as generally understood in the art, "microbial fuel cells" (i.e., MFCs) are fuel cells which operate by using microbes (i.e., microorganisms) that possess the ability to donate electrons to the anode of the fuel cell by the microbial oxidative degradation of compounds in order to produce electricity. Such microorganisms are known as exoelectrogenic organisms. Exoelectrogenic organisms can donate electrons to the anode in either of two ways: via mediators (e.g., the numerous dyes used in the art for this purpose) or in the absence of mediators (i.e., a mediator-less MFC).

An MFC contains an anode, a cathode, and typically, a porous material (e.g., a membrane) which separates an anode region (which contains the anode) from a cathode region (which contains the cathode). Typically, the porous material is in the form of a cation-selective permeable material (typically, a membrane). The anode and cathode are electrically connected by an electrical conductor (e.g., by a metal wire) held outside of the electrode solutions. The microorganisms in contact with the anode oxidatively catabolize the inhibitor compounds or materials described above to produce electrons and protons ($H^+$ ions), as well as oxidized organic material or carbon dioxide. The electrons are attracted to the anode and travel to the cathode. At the same time, the produced protons travel through the anodic solution and through the cation-selective permeable material to the cathode. At the cathode, oxygen gas (typically from air) reacts with the electrons and protons to produce water according to the reaction:

$$O_2 + 4H^{3O} + 4e^- \rightarrow 2H_2O$$

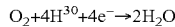

The cation-selective permeable material separating anodic and cathodic regions is also referred to herein as a cation exchange material. The cation-selective permeable material selectively allows the diffusion or passage of cations, such as hydrogen ions ($H^+$, otherwise referred to herein as "protons") while not allowing the passage of anions. The cation-selective permeable material should also substantially prevent oxygen from diffusing from the cathode side into the anode side. A particular type of cation-selective permeable material considered herein is a proton-selective permeable material. The cation-selective or proton-selective permeable material can be any such material known in the art having these properties. Typically, the cation- or proton-selective permeable material is in the form of a membrane, otherwise referred to herein as a cation- or proton-selective permeable membrane or cation or proton exchange membrane (PEM). Any of the PEMs known in the art can be used herein, such as, for example, those belonging to the class of ionomer polyelectrolytes having these properties, such as the Nafion® class of PEMs.

The MFC can have any suitable number of chambers for holding the anodic and cathodic portions of the process water. For example, the MFC may contain a single chamber wherein anodic and cathodic regions (e.g., solutions) are not separated. Alternatively, the anodic and cathodic media may be separated by an aqueous permeable membrane such as filter paper, cloth, or a specific molecular weight-cut off membrane, such as a 30 k Dalton cut-off membrane or 0.2 micron membrane. Alternatively, the MFC may contain two separate chambers, wherein the anodic and cathodic solutions are separated while being afforded ionic transport therebetween by, for example, a cation- or proton-selective salt bridge, or a glass bridge containing a cation or proton exchange membrane. In a preferred embodiment, the anode resides in the process water stream while the cathode is exposed to air or an oxidizing gas while also being in contact with the process water stream.

The anode can be constructed of any electrically conductive material known in the art suitable for the purposes described herein. The anode material is preferably amenable to the growth and adherence of microbes. Some classes of electrode materials or a coating thereof include conductive metals (e.g., silver, gold, titanium, cobalt, tungsten, stainless steel, and alloys thereof), conductive polymers, or a metal-deposited carbon anode (e.g., Fe-deposited carbon anode). Particularly preferred for the anode are electrodes based on conductive carbon. Typically, any structural form of carbon is suitable as a conductive carbon material. Some examples of carbon electrodes include carbon fiber, carbon paper, carbon foam (e.g., reticulated vitreous carbon), carbon cloth, carbon felt, carbon wool, carbon granules, carbon brushes, graphite, or a combination thereof. The conductive carbon material can have any suitable physical characteristics, such as having a porous, non-porous, powderized, grainy, fibrous, brush, nanotextured, or patterned texture. The conductive carbon material can also be of a less typical form of carbon, such as carbon nanotubes (e.g., single or double walled) or fullerenes. The anode can also have any of the three-dimensional architectures known in the art that are known to possess high porosity values and high flow-through rates. Alternatively, the anode can have a flat (e.g., planar or two-dimensional) topology.

The anode is preferably porous, and in particular, by having a porosity value of at least about 0.3 (and more preferably at least about 0.4, 0.5, 0.6, 0.7, 0.8, or 0.9), wherein the porosity value recited herein is calculated as the volume of void space over the total (i.e., bulk) volume. The foregoing porosity values can be recited as percentages (e.g., 0.3 corresponds to 30%). The anode also preferably possesses sufficient hydraulic conductivity such that the effluent can be processed in a manner that is commercially viable and efficient. For example, it is preferable for the anode to have a hydraulic conductivity of at least 0.5 cm/s, or 1.0 cm/s, or 5.0 cm/s, or 10 cm/s, or 20 cm/s, or 30 cm/s, or 40 cm/s, or 50 cm/s, or 60 cm/s, or 70 cm/s, or 80 cm/s, 90 cm/s, or 100 cm/s, or 110 cm/s, or 120 cm/s.

The anode can also have any suitable shape. The shape of the anode can be, for example, generally planar (e.g., 50 cm×50 cm×5 cm), block-shaped, columnar, spherical (e.g., 4 cm to 40 cm diameter), ovoid, or cuboidal (e.g., 1 cm×1 cm×1 cm or 20 cm×20 cm×20 cm). The anode can also be layered or segregated by containing layers or regions of the same or different anode materials.

For MFCs of the art, the ratio of the total volume of the anode (including void volume inside a porous anode) to the volume of the anode chamber (i.e., the "volume ratio") is typically within the range of 0.1 to 0.4. However, such small volume ratios are often not preferred since they are conducive to the growth of non-exoelectrogenic organisms. It has been found herein that use of higher volume ratios (i.e., greater than 0.4) advantageously encourage the growth of exoelectrogenic organisms. Accordingly, the method, as described herein, is preferably practiced by use of anode volume ratios of at least 0.5, more preferably at least 0.6, more preferably at least 0.7, more preferably at least 0.8, and even more preferably at least 0.9. Even more preferably, the volume ratio is approximately 1 (i.e., at or greater than 0.95), thereby attaining a dead volume of essentially zero in the anode chamber.

The surface area to volume ratio (specific surface area) for the anode can be any suitable value. As understood in the art, the anode volume being considered in calculating specific surface area includes the void space of the anode, and not the volume that the mass of the anode material itself occupies. The specific surface area is typically at least 50 $m^2/m^3$, and more preferably, at least 60 $m^2/m^3$, 70 $m^2/m^3$, 80 $m^2/m^3$, 90 $m^2/m^3$, 100 $m^2/m^3$, 150 $m^2/m^3$, 200 $m^2/m^3$, 250 $m^2/m^3$, 400 $m^2/m^3$, or 500 $m^2/m^3$. Generally, higher specific surface areas (i.e., preferably at least 1,000 $m^2/m^3$) improve the growth of exoelectrogenic organisms and increase power density during operation of an MFC for electricity or hydrogen production. In different embodiments, the higher specific surface area can be, for example, at least 5,000 $m^2/m^3$, at least 10,000 $m^2/m^3$, at least 30,000 m$^2$/m$^3$, at least 40,000 m$^2$/m$^3$, at least 45,000 m$^2$/m$^3$, or at least 50,000 m$^2$/m$^3$. High specific surface areas are preferably attained by use of a carbon felt or three-dimensional anode. Any ranges of specific surface areas resulting from any of the values set forth above are also contemplated herein.

Particularly in the case where the anode is constructed of a hydrophobic type of material (e.g., a carbon form), the anode can be rendered sufficiently hydrophilic to permit favorable interaction (i.e., adherence, interfacing, or bonding) of the anode material with aqueous media. The hydrophilicity can also serve to reduce or prevent agglomeration or sticking of hydrophobic compounds or materials (e.g., hydrophobic inhibitor compounds or inert materials) to the anode. Any method for coating the surfaces of the anode to render them sufficiently hydrophilic is applicable herein. For example, the anode surface can be powder-coated, spray-coated, or dip-coated with one or more hydrophilic polymeric or molecular materials, and optionally thermally processed, calcined, or dried. The anode can also be chemically treated by an oxidizing agent, such as ozone or hydrogen peroxide. The anode can also be treated by ionizing radiation or an ion beam process for this purpose. In a preferred embodiment, the anode is treated by a plasma process to render its surface hydrophilic. The plasma process is preferably an oxygen plasma process.

The cathode can be constructed of any suitable electrically conductive material, such as any of the materials described above for the anode. The cathode can also have any of the properties (e.g., porosity and hydraulic conductivity values) described above for the anode. In one embodiment, the cathode is any of the gas cathodes known in the art (e.g., a Pt/air electrode). Typically, the gas cathode contains a side which is immersed in the anodic liquid and another side exposed to the gas, which is typically air. The side exposed to the gas typically includes a cathode diffusion layer (CDL) which permits gas to enter but prevents leakage of anodic fluid. In another embodiment, the cathode is any of the ferricyanide electrode systems known in the art. In yet another embodiment, the cathode includes a biological system capable of transferring or utilizing electrons, e.g., a biocathode.

The spacing between the anode and cathode (i.e., the electrode spacing) can be any suitable spacing. In one embodiment, the spacing is within the range of 0 to 1 cm. Smaller electrode spacings (i.e., less than 1 cm) can also be used. For example, in different embodiments, the electrode spacing can be at about or less than 0.8 cm, or 0.5 cm, or 0.25 cm, or 0.1 cm, or 5 mm, or 4 mm, or 3 mm, or 2 mm, or 1 mm, or 0.5 mm. In another embodiment, the electrode spacing is greater than 1 cm, and can be, for example, at or greater than 2 cm, 5 cm, 10 cm, 20 cm, or 30 cm. The spacing between the electrodes can be at least partly determined by the thickness of the cation-permeable material separating the electrodes.

Preferably, in order to maximize electrical output and provide an efficient system for electricity production, the level of oxygen in the reaction zone of the anode is reduced, and preferably substantially reduced, so as to result in an appreciably anaerobic environment at the anode. Any method for removal and exclusion of oxygen at the anode can be used. In a preferred embodiment, nitrogen sparging of the anodic reaction zone is employed to render the anodic reaction zone substantially anaerobic.

The MFC described herein can have any suitable number of cathodes and anodes. For example, the MFC can be operated with one anode and more than one cathode, or one cathode and more than one anode, or an equivalent number of anodes and cathodes (e.g., two anodes and two cathodes, or three anodes and three cathodes). In addition, the MFC can function monolithically, or alternatively, in a stacked mode in which, for example, 2-250 MFC units are stacked in order to increase electrical power output. Other specifics and modifications known in the art of microbial fuel cell design can be found in, for example, U.S. Application Pub. No. 2007/0259217, which is incorporated herein by reference in its entirety.

The MFC is typically operated within a mild temperature range of about 20 to 50° C. and normal to elevated pressure conditions (i.e., approximately 1 atm or above). However, if thermophilic or hyperthermophilic organisms are used, the operating temperature of the MFC can be higher (e.g., at about or greater than 50° C., or 60° C., or 70° C., or 80° C., or 90° C., or 100° C.). In other embodiments, the MFC can be operated under cooler conditions of less than 20° C., such as a temperature of about or less than 15° C., or 10° C., or 5° C., or 4° C., or 2° C. Operating temperatures of 0° C. or lower are possible depending on the ionic strength or molarity of the process water.

In one embodiment, the microbes (or a portion thereof) interacting with the anode are planktonic, i.e., flotational. However, planktonic microbes are susceptible to being lost into process waters, particularly if the process water is flowing at an appreciable rate. To prevent the loss of the microbes into process water, the planktonic microbes can be contained in a compartment which is permeable to the inflow and outflow of the process water and which is non-permeable to the microbes.

In another embodiment, the microbes (or a portion thereof) reside on the anode in the form of a biofilm (i.e., non-planktonic film or mass of microbes). For the purposes of the present invention, a biofilm is preferable since microbes in a biofilm adhere to the anode surface, and are thus significantly less prone to being drawn (and lost) into the process water. A biofilm of microbes can remain in place with substantially no loss of microbes even at high flow rates.

A biofilm of microbes can be established using any of the methods known in the art. For example, as known in the art, a biofilm of microorganisms can be produced on an anode by initiating a colony of microbes on the anode (i.e., by contact of the anode with the microbes under suitable thriving conditions) and then growing the colony until a biofilm is established on the anode. Preferably, in order to favor growth of exoelectrogenic microbes, the initiation and growth stage is conducted on the anode while the anode is in electrical communication with the cathode. In this way, electrons being donated to the anode from exoelectrogenic microorganisms can be conducted to the cathode.

The biofilm can be initiated by contact of the anode with an anolyte (i.e., either a specially prepared anodic medium or process water) that has been inoculated with a sampling of microorganisms, at least a portion of which should be capable of operating by an exoelectrogenic mechanism. Preferably, at some point either at the time of contact, or after contact of the anode with the microorganisms in the anolyte, forced flow and recirculation conditions (i.e., as provided by a pump) are established for the anolyte. For example, in the case of a porous anode, the anolyte is made to flow and recirculate through the anode. A significant portion of microorganisms that do not have a strong propensity for forming biofilms, even though they may be initially associated with the biofilm, will be driven into the anolyte by the flow force. Accordingly, the forced flow and recirculation conditions of the anolyte serve to enrich the biofilm with microorganisms that have a strong propensity for forming biofilms.

In turn, microorganisms with a strong propensity for forming biofilms are more likely to contain pili (nanowires) on their external membrane which can also be used by the microorganisms for direct electron transfer to the anode. Therefore, the forced flow and recirculation conditions of the anolyte can also serve to further enrich the biofilm with exoelectrogenic microorganisms capable of direct electron transfer. At least one advantage of enriching the biofilm with exoelectrogenic microorganisms capable of direct electron transfer is that mediators (e.g., ferric oxides, neutral red, anthraquinone dyes, 1,4-napthoquinone, thionine, methyl viologen, methyl blue, humic acid, ABTS, and the like) are less needed or completely not needed for facilitating electron transfer. A mediator-less system is advantageous in that not only are mediators typically expensive, often toxic, and require replenishment, but mediated electron transfer is typically less efficient than direct (mediator-less) electron transfer.

Preferably, in preparing a biofilm on the anode, the flow rate of the anolyte should be high enough to at least maintain planktonic microorganisms floating in the medium such that they can be eliminated. A suitable flow rate can be, for example, at least about 2 or 3 mL/min. In different embodiments, the flow rate can be either substantially constant or fluctuating within a range of, for example, 2-10 mL/min, or 3-10 mL/min, or 4-10 mL/min, or 5-10 mL/min, or 6-10 mL/min, or 3-8 mL/min, or 3-7 mL/min, or 4-8 mL/min, or 4-7 mL/min. The foregoing flow rates are preferably no more than 10 mL/min and are thus herein referred to as a "low flow rate".

More preferably, in preparing a biofilm on the anode, the flow rate is high enough to render those biofilm-forming microorganisms with a residual level of planktonic ability (i.e., semi-planktonic microorganisms) waterborne (i.e., flotational), and thus, removable, as further described below. This higher flow rate is preferably above 10 mL/min. In different embodiments, the flow rate can be, for example, at least about 12 mL/min, or at least about 15 mL/min, or at least about 20 mL/min, or at least about 25 mL/min, or at least about 30 mL/min, or at least about 35 mL/min, or at least about 40 mL/min, or at least about 45 mL/min, or at least about 50 mL/min. In different embodiments, the higher flow rate can be either substantially constant or fluctuating within a range of, for example, 12-60 mL/min, 12-50 mL/min, 12-40 mL/min, 12-30 mL/min, 12-20 mL/min, 15-60 mL/min, 15-50 mL/min, 15-40 mL/min, 15-30 mL/min, 15-20 mL/min, 20-60 mL/min, 20-50 mL/min, 20-40 mL/min, 20-35 mL/min, 20-30 mL/min, 25-60 mL/min, 25-50 mL/min, 25-40 mL/min, 25-35 mL/min, 25-30 mL/min, 30-60 mL/min, 30-50 mL/min, 30-40 mL/min, 35-60 mL/min, 35-50 mL/min, 35-40 mL/min, 40-60 mL/min, 40-50 mL/min, 45-60 mL/min, 45-50 mL/min, or 50-60 mL/min.

To reflect changes in volume and cross-sectional area of the MFC (i.e., anode), the flow rate can alternatively be represented in terms of space velocity (cm/min) or hydraulic retention time (HRT in units of minutes). To convert flow rates given in units of mL/min into space velocity, the flow rates are divided by the cross-sectional area of the MFC. For example, for a MFC having a cross-sectional area of 1.25 cm$^2$, a flow rate of 2 mL/min corresponds to a space velocity of approximately 1.6 cm/min; a flow rate of 10 mL/min corresponds to a space velocity of 8 cm/min, and a flow rate of 30 mL/min corresponds to a space velocity of 24 cm/min. To convert flow rates given in mL/min into HRT values, the flow rate is inserted into the following equation: HRT=(volume of chamber)/(flow rate in mL/min). For example, for a MFC having a chamber volume of 13.25 mL, a flow rate of 2 mL/min corresponds to a HRT value of approximately 6.6 min.; a flow rate of 10 mL/min corresponds to a HRT value of approximately 1.3 min, and a flow rate of 30 mL/min corresponds to a HRT value of approximately 0.44 min.

In a preferred embodiment for preparing a biofilm on the anode, the anolyte is made to flow at any of the low flow rates or ranges thereof, described above, on a continuous basis (and either a substantially constant or fluctuating basis) along with periodic, intermittent, or occasional interruptions by any of the higher flow rates or ranges thereof described above. For example, in one embodiment, a continuous low flow rate in the range of 2-10 mL/min is periodically interrupted by a higher flow rate. The higher flow rate is preferably any of the higher flow rates described above, and more particularly, a flow rate greater than 10 mL/min, and more preferably, a flow rate of or greater than 12 or 35 mL/min. In a particularly preferred embodiment, the higher flow rate is at least about 35 mL/min. In another embodiment, a continuous low flow rate in the range of 3-10 mL is periodically interrupted by a higher flow rate in the range of 30-40, 30-50, or 40-50 mL/min. In another embodiment, a continuous low flow rate in the range of 3-7 mL is periodically interrupted by a higher flow rate in the range of 30-40, 30-50, or 40-50 mL/min.

During the forced flow and recirculation conditions for preparing a biofilm on the anode, planktonic microorganisms (i.e., those having a propensity to float in solution rather than form a biofilm) are substantially removed by a suitable process (e.g., by use of a syringe or flushing into the effluent water). Preferably, any chemicals that may function as mediators are also removed. For example, in a preferred embodiment, planktonic microorganisms are removed by the periodic replacement of all or a portion of the flowing and recirculating anolyte. Since the majority of planktonic microorganisms and any mediators float in solution, periodic replacement of the anolyte functions to remove these species.

In different embodiments for preparing a biofilm on the anode, the anolyte may be replaced, either by a set or arbitrary number of times of equivalent volumes of anolyte, or by a set or arbitrary rate of replacement such that a substantial absence of planktonic microorganisms in the anolyte in contact with the anode is realized. Preferably, a substantial absence of planktonic microorganisms corresponds to at least about 80%, more preferably at least about 85%, more preferably at least about 90%, and even more preferably at least about 95% reduction in concentration of planktonic microorganisms in the flowing and recirculating anolyte. For example, in one embodiment, the anolyte is substantially replaced by 1-20 equivalent volumes of anolyte, either at set intervals or in an arbitrary manner. In another embodiment, the anolyte is substantially replaced (i.e., at least 90% replaced by volume for each instance of replacement) at specific intervals, such as every few minutes, hours, or days. Alternatively, the anolyte can be replaced when an optical transmission parameter (property) of the anolyte reaches a level indicative of the presence of planktonic microorganisms. For example, a turbidity analyzer (e.g., by laser scattering) or optical density instrument can be used to measure the relative turbidity or light transmission of the anolyte. In a preferred embodiment, the anolyte is replaced whenever the recirculating anolyte reaches an optical density (e.g., $OD_{600}$) threshold, e.g., above 0.05 units. Replacement of the anolyte can then be stopped when the optical density value no longer exceeds the desired threshold level.

In a preferred embodiment for preparing a biofilm on the anode, anolyte is replaced directly after the anolyte is subjected to a high flow rate pulse. In this case, the high flow rate pulse can be conducted either during recirculation of the anolyte, or alternatively, during a momentary interruption of the recirculation condition for a time sufficient for the high flow rate pulse (and optionally, a simultaneous or subsequent removal of the medium used for the high flow rate pulse) to take place. The medium used in the high flow rate pulse can be the medium being recirculated or can be a separate medium (e.g., water, purified water, buffered water, or mineralized water) not in contact with the recirculated medium. In a particular embodiment, the pressure resulting from the high flow rate pulse is used to force the medium out of an outlet of the anodic chamber so that the medium used in the high rate pulse is immediately ejected from the anodic chamber after the high flow rate pulse.

In one embodiment, the microbes residing on the anode have an innate ability to efficiently consume one or more inhibitor compounds known to be present in the process water. The microbes may, in addition, be capable of consuming non-inhibitor compounds or materials that may also be present in the process water. In such a case, the microbes may be used in the treatment process without first cultivating and enriching the microbes on inhibitor-containing anolyte or process water.

In another embodiment, the initial microbe population may not include a sufficient number of microbes that possess an ability to effectively or efficiently consume one or more inhibitor compounds. In such a case, the microbes are preferably cultivated on one or more inhibitor compounds as a nutrient source in order to select and enrich those microbes that possess a tendency or ability to consume inhibitor compounds. The inhibitor compounds selected as a nutrient source are preferably the same (or chemically similar) as the inhibitor compounds to be removed from the effluent. By cultivating microbes on one or more inhibitor compounds, those microbes having a propensity or inclination to catabolize inhibitor compounds undergo a growth stage while microbes not so inclined become weakened by malnutrition and are eventually eliminated from the consortium. In this way, a consortium of microbes enriched in inhibitor-consuming microbes is produced.

The above microbial growth and enrichment stage is preferably achieved by contacting a microbe-laden anode with a solution containing one or more inhibitor compounds or materials. The inhibitor compounds or materials can be administered as a sole nutrient source, or along with other nutritive compounds. Alternatively, the microbes may be initially fed a diet based solely or predominantly on one or more traditional nutritive compounds and thereafter fed a diet more highly concentrated in inhibitor compounds. The transition from a diet based predominantly on non-inhibitor compounds to one based predominantly on inhibitor compounds can be sudden, incremental, or continuously gradual. The non-inhibitor nutritive compounds are any compounds or materials that can be oxidatively degraded by exoelectrogenic microorganisms such that electrons and protons result from the degradation. The non-inhibitor nutritive compounds can broadly include, for example, waste products (e.g., from sewage streams, industrial pollutants and byproducts, and foodstuffs), synthetic and natural compounds, plastics, and polymers, and biological materials. Typically, the non-inhibitor nutritive compounds are biodegradable. The non-inhibitor nutritive compounds can be selected from, for example, higher carboxylic acid-containing compounds or materials (e.g., butyric, valeric, caproic, caprylic, capric, undecanoic, dodecanoic, tridecanoic, and myristic acids, or vegetable- or animal-based fatty acids), carbohydrate compounds or materials (e.g., monosaccharides, disaccharides, oligosaccharides, and polysaccharides), lipid-containing substances (e.g., fats, mono-, di-, or triglycerides, oils, fatty acids, lipoproteins, or liposaccharides), amino acid-containing substances (e.g., amino acids, dipeptides, tripeptides, oligopeptides, or proteins), or a combination thereof. The growth medium can also contain one or more inorganic compounds or materials, such as minerals and vitamins, e.g., alkali and alkaline halide salts (e.g., KCl, $MgCl_2$, and the like), phosphates, ammonium salts, and the like.

The growth stage is preferably conducted by administration of an excess amount of the nutritive source. An excess amount of nutritive source, as used herein, is an amount exceeding the amount required for producing the maximum level of current achievable under the conditions (e.g., resistance, and other factors) provided by the MFC, such that the excess amount can be used by the microorganisms to grow and multiply in numbers. As further described below, an excess amount of nutritive source can be advantageous by encouraging the biofilm microorganisms to store carbon internally during a subsequent state of famine.

The microbial growth stage is preferably continued until an electrical current output of the MFC becomes level at a fixed resistance between the anode and cathode, after which time the nutritive compounds can be withheld for a suitable period of time, or periodically administered, in order to maintain a desired current or voltage level. For example, the growth stage may be considered complete when the electrical output of the MFC stabilizes to a voltage between 0.3-0.4 V at a 500 ohm load. Any of the non-inhibitor nutritive sources (e.g., sugars) described above can also be used periodically or continuously as a nutritive supplement during the treatment process by the MFC.

The microorganisms (either in biofilm or planktonic form) can also be subjected to a starvation stage. A starvation stage serves two main purposes: i) to enrich the microorganisms with organisms having internally stored carbon by eliminating those organisms that are incapable of internally storing carbon for their cellular maintenance and electricity production during the starvation stage, and ii) to enrich the microorganisms with a higher proportion of exoelectrogenic microorganisms by weakening non-exoelectrogenic organisms and eliminating them. Preferably, the starvation stage is conducted after formation of a biofilm and more preferably after a growth stage, as described above. During the starvation stage, organisms that lack the ability to store carbon internally will weaken and be eliminated due to an absence of a food source for such organisms. Conversely, those organisms having an inclination for carbon storage will thrive under such conditions.

The starvation stage is preferably conducted by lowering the administered amount of organic nutritive compound in the anolyte to below the amount required for the microorganisms to produce the maximum achievable current under the conditions (e.g., resistance, and other factors) provided by the MFC. The amount of nutrient required to produce the maximum achievable current under conditions provided by the MFC is hereinafter referred to as the "nutrient threshold value". Preferably, the administered amount of organic nutritive compound (i.e., nutrient) during the starvation stage is no more than 50% of the amount required to attain the nutrient threshold value. More preferably, the administered amount of nutrient during the starvation stage is no more than 25%, or no more than 10%, or no more than 1%, of the amount required to attain the nutrient threshold value. In a particularly preferred embodiment, the administered amount of organic nutritive compound is substantially eliminated from the anolyte. By being "substantially eliminated" from the anolyte is meant that nutritive organic compounds are not administered in any amount, except that residual amounts of organic nutritive compounds (e.g., generally under 1% of threshold level) may be present. The starvation stage is preferably conducted for a period of time until the biofilm is enriched in microorganisms capable of storing carbon internally. Enrichment of the biofilm with carbon-storing microorganisms is typically evidenced by maintenance of the voltage output of the MFC during the starvation stage. A decline of the voltage occurs when the carbon stores in the microorganisms become depleted to a level under the level required to maintain the voltage. Preferably, after the initial indication of a voltage decline, the starvation stage is ended by administration of an amount of organic nutrient sufficient to at least maintain the voltage of the MFC. However, the starvation stage can be ended before a voltage decline is observed, i.e., at a point in time for which it is known that a certain level of enrichment has occurred.

The microorganisms (either in biofilm or planktonic form) can also be subjected to a decreased electrical resistance stage. Lowering the resistance (i.e., load) across the anode and cathode increases the current flow between the two electrodes, and this in turn encourages the growth of exoelectrogenic organisms (i.e., further enrichment of the microorganisms with exoelectrogenic organisms). Preferably, the electrical resistance is lowered after any of the stages described above for producing a biofilm, and more preferably after the starvation stage described above (and more preferably, with reinitiation of the supply of the organic nutritive compounds). The external resistance is typically controlled by use of a resistor box. The resistor box is preferably one which can be set to any suitable resistance, preferably within the range of 0-5000 ohms. The resistance can be reduced by any desirable or suitable amount, either in discrete amounts or gradually over a desired period of time. For example, in different embodiments, the load can be decreased to about 95%, or 90%, or 85%, or 80%, or 75%, or 70%, or 65%, or 60%, or 55%, or 50%, or 45%, or 40%, or 35%, or 30%, or 25%, or 20%, or 15%, or 10%, or 5% its original (or full capacity) value. The MFC, preferably containing a biofilm and optionally pre-processed by one or more of the steps described above, is then contacted with process water such that microbes residing at the anode oxidatively degrade inhibitor materials contained therein while producing electricity.

The electrical power output of the MFC in terms of anode surface area (i.e., the area power density) is preferably at least 2,000 mW/m$^2$, and more preferably, at least 2,500 mW/m$^2$, or 3,000 mW/m$^2$, or 3,500 mW/m$^2$, or 4,000 mW/m$^2$, or 4,500 mW/m$^2$. The area power density can be converted to volumetric power densities (in units of W/m$^3$) by multiplying the area power density by the ratio of the projected anode or membrane area to the total volume of the anode (i.e., in m$^2$/m$^3$) and 1/1000. Discussion and examples of specific surface area have been given above. For lower area to volume ratios, some values of volumetric power density include, for example, 100, 200, 300, 400, 500, 600, 700, 800, 900, or 1,000 W/m$^3$, or a range resulting from any two of these values. For higher area to volume ratios, some values of volumetric power density include, for example, 2,000, 5,000, 10,000, 20,000, 50,000, 100,000, 150,000, or 200,000 W/m$^3$, or a range resulting from any two of these values. Typically, the volumetric power density is recited in terms of net anode volume (NAV), which is the void volume fraction (i.e., volume fraction occupied by liquid) in the anode. To convert the volumetric power density to reflect the NAV, the volumetric power density is divided by the void volume ratio, which has the effect of increasing the value of the volumetric power density. Typically, the NAV is at or above 25% and up to about 95% (i.e., typically any value within 0.25 to 0.95). Some NAV values include, for example, 25%, 30%, 35%, 40%, 45%, 50%, 55%, 60%, 65%, 70%, 75%, 80%, 85%, 90%, and 95%, or values above or below any of these values, or any range resulting from any two of these values.

The method can also be practiced by modifying the process water before, during, or after processing by the MFC. The modification of the process water can, for example, enhance or promote MFC operation as compared to MFC operation using unmodified process water.

In one embodiment, the process water is modified by being diluted. Dilution can be particularly beneficial for a case wherein an MFC is either intolerant of a specified inhibitor concentration or functions non-optimally above a specified (i.e., critical) total or individual inhibitor concentration. The MFC can be intolerant of or function non-optimally in a total or individual inhibitor concentration of or less than, for example, any of the exemplary inhibitor concentrations given above. Dilution can also be particularly beneficial for a case wherein an MFC is either intolerant of (or functions non-optimally above) a specified concentration of one or more non-inhibitor compounds or materials. Process water that has been treated by the MFC can also be diluted if a further reduction in the concentration of one or more inhibitors or other materials is desired.

In another embodiment, process water is concentrated before entering the MFC or after exiting the MFC. The process water can be concentrated by, for example, evaporation. If desired, the evaporated water can be recaptured by a condensation process, and the condensed water recycled into the process (or used for a different process or as a commodity). In a preferred embodiment, the electrical power being generated by the same or different MFC can be directed to power the evaporation process (i.e., by directing the electricity to produce heat). Feeding concentrated process water to a MFC is particularly applicable for a case in which the MFC has a tolerance for high concentrations of inhibitors, or when higher electrical outputs are desired.

In yet another embodiment, the process water is modified by the addition thereto of one or more additional nutritive compounds. The additional nutritive source can include, for example, sugars, organic acids, or other nutritive source.

In yet another embodiment, the process water is modified by the removal of one or more compounds or materials residing therein before feeding the process water to the MFC. For example, fermentation process water can be treated by a process that reduces the level (or removes) one or more compounds or materials therein before the process water enters the MFC. The one or more compounds or materials can be desirably removed for any reason that benefits the process, and particularly, if the one or more compounds have a deleterious affect on the MFC, or if the one or more compounds are not effectively degraded by the MFC and interfere with an aspect of the process. Some removal processes include chemical or physical oxidation, reduction, precipitation, adsorption, degradation, or filtration. However, the removal process does not dispense of the need for the MFC to remove one or more inhibitors. The process relies on the MFC for at least the partial removal of at least one inhibitor compound or material.

Process water that has been treated by a MFC can also be further processed to remove one or more compounds generally not processable by the MFC. The one or more compounds or materials being removed can be, for example, oxidation products of inhibitor or other compounds that have been oxidatively degraded by the MFC. In one embodiment, the removal process is provided by any of the chemical or physical removal processes described above. In another embodiment, the oxidation products exiting a MFC (incapable of further processing the oxidation products) are fed to another MFC capable of consuming the one or more oxidation products.

In still another embodiment, an oxidation pre-treatment step (i.e., pre-oxidation treatment step) is employed on the process water before the process water is fed to the MFC. An oxidation pre-treatment step can be particularly useful for initiating the oxidation of oxidatively resistant (i.e., recalcitrant) inhibitor (or other) compounds, such as the aromatic compounds. By employing the oxidation pre-treatment step, recalcitrant organic compounds that may be difficult or impossible for the microbes to oxidatively degrade can be more easily and more completely degraded. The oxidation pre-treatment step can use any oxidant known in the art capable of oxidizing recalcitrant organic compounds to a level sufficient for further processing by the MFC. Preferably, the oxidant is environmentally benign. The oxidant can be, for example, ozone, a peroxide, a halogen-oxide compound, or nitrogen-oxide compound. Alternatively, the oxidation pre-treatment step is a physical process, such as a thermal, electrolytic, or radiative process. The oxidation process (e.g., ozonation) typically oxidizes the organic compound to a more highly oxygenated compound.

In still other embodiments, the process water is modified by heating, cooling, filtration, precipitation, reduction, electrolysis, pH adjustment, emulsification, chemical treatment, anaerobic digestion (e.g., gasification or methane-conversion of inhibitor compounds or other compounds), or other process. The process water can be treated by one or a combination of such processes on entering an MFC or exiting an MFC. Any of the foregoing processes can be powered (or partly powered) by electrical power generated by one or more MFCs that are consuming inhibitors (and optionally, other compounds) in the process.

The MFC can also be operated in a manner such that the cathode of the MFC, instead of producing water by absorption of oxygen, produces hydrogen gas. In order to render the MFC capable of producing hydrogen gas, the MFC is preferably modified in one or more ways, as follows: i) the cathode is preferably constructed of a hydrogen-producing material; ii) the cathode is preferably substantially deoxygenated; and iii) the cell potential of the MFC is preferably adjusted, by application of an external voltage, such that hydrogen can be produced at the cathode. When hydrogen is produced, such a device can be referred to herein as a microbial electrolysis cell (MEC).

The hydrogen-producing material of the cathode can be any material capable of producing hydrogen from protons, including, for example, hydrogen-producing metals, such as typically platinum (Pt), palladium (Pd), nickel (Ni), iron (Fe), copper (Cu), or an alloy thereof. Other possible hydrogen-producing materials include hydrogen-producing enzymes or microbes. An anaerobic environment at the cathode may be provided without special measures if the conditions in which the MFC is employed are naturally anaerobic, e.g., in the case of anaerobic fermentation where an anaerobic environment is maintained on process water directed to the MFC. However, if anaerobic conditions are not naturally present, deoxygenation of the cathode can be conveniently achieved by, for example, sparging of the catholyte with nitrogen (or other inert gas) and/or sealing of the cathodic chamber so as to prevent entry of air. The cell potential ($\Delta V$) can be adjusted such that the MFC anode potential (typically around $-0.3$ V vs. SHE (standard hydrogen electrode potential)) is externally supplemented such that the potential difference between the anode and the cathode is at least about 0.41 V. For example, the anode can be externally assisted with a voltage of about 0.11 to 0.25 V or higher for this purpose, depending on the magnitude of the cathode overpotential. For hydrogen production, the anolyte and catholyte need not be separated by a cation-permeable or cation-selective permeable membrane. Other specifics and modifications known in the art for configuring a microbial fuel cell to operate by producing hydrogen can be found in, for example, U.S. Application Pub. No. 2008/0277272, which is incorporated herein by reference in its entirety.

The produced hydrogen gas can be used for any purpose, e.g., as a commodity chemical, a reactant or processing chemical in the cellulosic ethanol process (or other process), as a fuel source (particularly for powering one or more processes in the cellulosic ethanol process), or as a chemical reactant for the production of one or more chemical products. As a reactant in the process, the hydrogen gas can be used for hydrogenation, or as part of a reductive process, for inhibitor or other compounds. As a fuel source, the hydrogen gas can be combusted with a reactive (i.e., oxidizing) gas, or reacted with a gas to produce a fuel which is then combusted, e.g., the physical-, enzymatic-, or microbial-mediated production of methane (natural gas) from syngas (i.e., $CO+H_2$). As a processing chemical, the hydrogen gas can be used to promote an anaerobic environment in any part of the MFC or in the fermentation process. As a chemical reactant, the hydrogen gas can be used in, for example, a Fischer-Tropsch process for the production of hydrocarbons (e.g., alkanes).

In a particular embodiment, the produced hydrogen is used as an electricity-generating fuel to power one or more processes, particularly one or more process steps in the cellulosic ethanol process. By one method, the produced hydrogen is used as a feedstock for another MFC capable of consuming hydrogen for the production of electricity. By another method, the produced hydrogen is directed into a non-microbial fuel cell (e.g., hydrogen-oxygen fuel cell) capable of reacting hydrogen with a suitable oxidant (typically oxygen) to produce water while generating electricity. The fuel cell can be any suitable fuel cell known in the art capable of reacting hydrogen gas with an oxidant to make electricity. The fuel cell can be, for example, a hydrogen-oxygen proton exchange membrane (PEM) fuel cell, an alkaline fuel cell, metal hydride fuel cell, molten carbonate fuel cell, or solid oxide fuel cell.

The MFC can also be operated in a manner such that one or more electrochemically reducible compounds or materials is reduced at the cathode. Preferably, the cathode of the MFC is operated in the substantial absence of oxygen for this purpose. The reductive process is preferably used for the breakdown or elimination of one or more chemical species that are deleterious to the MFC or the process (e.g., inhibitors), or that are environmentally malignant. The environmentally malignant species can be, for example, a degradation product, pollutant, waste product, or toxin. Some examples of reductive processes include nitrate reduction, perchlorate reduction, and heavy metal reduction (Rabaey, K. et al. *The ISME Journal* 1, 9-18 (2007)).

In one embodiment, the reducible species is a compound or material containing a nitrogen oxide (N—O) bond. Such a compound is commonly a nitrate-containing species (i.e., "a nitrate" or "nitrate compound"). The nitrate compounds can include inorganic nitrate species (e.g., $NaNO_3$, $KNO_3$, $NfLNO_3$, $Mg(NO_3)_2$, $AgNO_3$, $HNO_3$, and so on) as well as organonitrate species, such as tetramethylammonium nitrate. Other types of nitrogen oxide compounds that can be reduced include the nitrites, organonitro compounds, dinitrogen tetroxide, nitrosyl (nitroso) compounds, nitric oxide (NO), and nitrosonium species.

In another embodiment, the reducible species is a compound or material containing a halogen oxide bond. A common class of such compounds are the chlorine oxide class of compounds. A common subclass of chlorine oxide compounds are the perchlorates. The perchlorates include inorganic perchlorate species (e.g., $LiClO_4$, $NaClO_4$, $KClO_4$, $NH_4ClO_4$, $Mg(ClO_4)_2$, $AgClO_4$, $HClO_4$, and so on) as well as organoperchlorate species, such as tetramethylammonium perchlorate. Other subclasses of chlorine oxide compounds include the chlorates, chlorites, hypochlorites, and their acids. Other classes of halogen oxide compounds include the bromine oxide and iodine oxide classes of compounds. Some subclasses of bromine oxide compounds include the perbromates, bromates, bromites, hypobromites, and their acids. Some subclasses of iodine oxide compounds include the periodates, iodates, iodites, hypoiodites, and their acids.

In another embodiment, the reducible species is a compound (e.g., salt) or material containing one or more reducible metal species. A reducible metal species typically contains a metal atom having a positive oxidation state. The reductive method is particularly effective in reducing heavy metals, which are often harmful to the environment and in need of removal. Some examples of reducible metal species include Cr(VI) as found in chromates and dichromates, Mn(VII) as found in permanganates, Fe(III), Ni(III), Cu(II), Cu(I), Pd(II), Ag(I), Cd(II), Au(II), Au(I), Hg(I), Pb(II), and U(VI), which can be converted to the relatively insoluble U(III) species. The more reducible heavy metals can be reduced to elemental form, which can allow for their more facile removal.

In yet another embodiment, the reducible species is a peroxide. The peroxide can be, for example, inorganic (e.g., hydrogen peroxide), or an organoperoxide, such as carbamide peroxide, dibenzoyl peroxide, and cumene hydroperoxide.

In still another embodiment, the reducible species is a reducible sulfurous substance. The sulfurous substance can be, for example, sulfur dioxide, sulfur trioxide, sulfuric acid, a sulfate, a sulfite, a bisulfite, a persulfate (e.g., a peroxodisulfate), or a disulfide.

In one embodiment, the invention is practiced using one MFC. In another embodiment the invention is practiced using two or more MFCs. In one case, the two or more MFCs can be used to treat the same process water (i.e., process water emanating from the same process step). In another case, the two or more MFCs can be used to treat different process waters (i.e., process waters emanating from different process steps). In addition, regardless of whether the multiple MFCs treat the same or different process waters, the MFCs can perform the same or different tasks (e.g., removal of the same or different inhibitor compounds).

In a first embodiment, a first MFC (or system of MFCs) generates electrical energy (or hydrogen) from the consumption of one or more non-inhibitor compounds or materials while a second MFC (or system of MFCs) generates electrical energy (or hydrogen) from the consumption of one or more inhibitor compounds or materials. Such an embodiment can be particularly useful in a situation where microbes of the first MFC are adept at consuming non-inhibitor compounds (and non-adept in consuming inhibitor compounds) while microbes of the second MFC are adept at consuming inhibitor compounds (and non-adept in consuming non-inhibitor compounds). In one case, the one or more non-inhibitor compounds are produced in the cellulosic ethanol process, and can include, for example, sugars, oligosaccharides, polysaccharides, lignin, ethanol, sugar degradation products, or derivatives or modified forms thereof. Process water containing non-inhibitor compounds can emanate from any process step in which these compounds are produced or are present, e.g., during pretreatment, saccharification, fermentation, or distillation. In another case, the one or more non-inhibitor compounds are not produced in the cellulosic ethanol process, but are instead provided to the MFC either by adding them to the process water, or as a separate solution (i.e., not as process water) fed to the MFC.

In a second embodiment, a first MFC (or system of MFCs) generates electrical energy (or hydrogen) from the consumption of one or more inhibitor compounds or materials while a second MFC (or system of MFCs) generates electrical energy (or hydrogen) from the consumption of one or more other (i.e., different) inhibitor compounds or materials. Such an embodiment can be particularly useful in a situation where microbes of the first MFC are adept at consuming one or more types of inhibitor compounds (and non-adept in consuming one or more other types of inhibitor compounds) while microbes of the second MFC are adept at consuming one or more other types of inhibitor compounds that the first MFC is non-adept at consuming.

The electrical power (or hydrogen) generated by one or more MFCs of the process is preferably directed to the operation of one or more processes in the cellulosic ethanol process. For example, the produced electrical power (or hydrogen) can be used to power a heating step. Some examples of heating steps that can be accordingly powered include heating of fermentation process water, separation (e.g., by distillation or pervaporation) of ethanol from the fermentation process water, heating to remove water from unconverted biomass, heating of an anaerobic digester unit (for gasification or methane conversion of inhibitor compounds and/or other compounds), steam production, steeping, or boiling.

The microorganisms (i.e., organisms) that are used in the MFC can be any suitable microorganisms. The microorganism can be, for example, eukaryotic or procaryotic, and either unicellular or multicellular. An example of a suitable unicellular eukaryotic microorganism is yeast. Other examples of unicellular eukaryotic microorganisms include the protists or protozoans, such as amoeba and paramecia. An example of multicellular eukaryotic microorganisms includes the euglena. Those algae capable of uptake of organic carbon (e.g., eukaryotic or procaryotic mixotrophic forms) are also contemplated herein. Procaryotic organisms are predominantly unicellular, and are divided into two domains: the bacteria and the archaea. The procaryotic organisms can also be broadly divided into four main groups according to their shape: the cocci, the bacilli, spirilla, and vibrio. The archaea include the extremophiles (e.g., as found in hot springs and lakes), and the non-extremophiles, as found in soil, the oceans, and marshland. The archaea also include the methanogens.

In one embodiment, the microorganisms considered herein are bacteria. Some examples of phyla of bacteria considered herein are the Acidobacteria, Actinobacteria, Aquificae, Bacteroidetes, Chlorobi, Chlamydiae/Verrucomicrobia, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria ($\alpha$, $\beta$, $\gamma$, $\delta$ varieties), Spirochaetes, Synergistetes, Tenericutes, Thermodesulfobacteria, Thermotogae, or any combination thereof. Some particularly relevant families of bacteria being considered herein include Acidaminococcaceae, Acidobacteriaceae, Aeromonadaceae, Alteromonadaceae, Clostridiaceae, Comamonadaceae, Desulfobulbaceae, Desulfiromonadaceae, Enterobacteriaceae, Geobacteraceae, Pasturellaceae, Pelobacteraceae, Pseudomonadaceae, Rhodocyclaceae, and Shewanellaceae. Any combination of bacteria containing at least one of the above families of bacteria are also contemplated herein.

In a particular embodiment, the microbes include bacteria from the phylum Firmicutes. Some particular classes of Firmicutes bacteria being considered herein are Bacilli, Clostridia, and Mollicutes. A particular order of Clostridia being considered herein is Clostridiales. Some particular families of Clostridiales being considered herein are Acidaminococcaceae, Clostridaceae, and Veillonellaceae. Some particular genera of Acidaminococcaea or Veillonellaceae being considered herein are Acetonema, Acidaminococcus, Allisonella, Anaeroarcus, Anaeroglobus, Anaeromusa, Anaerosinus, Anaerovibrio, Centipeda, Dendrosporobacter, Dialister, Megamonas, Megasphaera, Mitsuokella, Pectinatus, Pelosinus, Phascolarctobacterium, Propionispira, Propionispora, Quinella, Schwartzia, Selenomonas, Sporomusa, Sporotalea, Succiniclasticum, Succinispira, Thermosinus, Veillonella, and Zymophilus. Some particular genera of Clostridaceae being considered herein are Acetanaerobacterium, Acetivibrio, Acidaminobacter, Alkaliphilus, Anaerobacter, Anaerotruncus, Anoxynatronum, Bryantella, Caldanaerocella, Caloramator, Caloranaerobacter, Caminicella, Candidatus Arthromitus, Clostridium, Coprobacillus, Dorea, Ethanologenbacterium, Faecalibacterium, Garciella, Guggenheimella, Hespellia, Linmingia, Natronincola, Oxobacter, Parasporobacterium, Sareina, Soehngenia, Sporobacter, Subdoligranulum, Tepidibacter, Tepidimicrobium, Thermobrachium, Thermohalobacter, and Tindallia.

In another particular embodiment, the microbes include one or more classes of bacteria from the phlyum Proteobacteria.

A particular class of Proteobacteria being considered herein is Alpha Proteobacteria. Some particular orders of Alpha Proteobacteria being considered herein are Caulobacterales (e.g., the family Caulobacteraceae, or *Caulobacter* sp.), Kordiimonadales, Parvularculales, Rhizobiales (e.g., the family Rhizobiaceae, or *Rhizobium* sp.), Rhodobacterales, Rhodospirillales (e.g., the family Acetobacteraceae, or *Acetobacter* sp.), Rickettsiales (e.g., the family Rickettsiaceae, or *Rickettsia* sp.), and Sphingomonadales (e.g., the family Sphingomonadaceae, or *Sphingomonas* sp.), wherein "sp." or "spp." as used herein both indicate one or more species of the indicated genus.

Another particular class of Proteobacteria being considered herein is Beta Proteobacteria. Some particular orders of Beta Proteobacteria being considered herein are Burkholderiales, Hydrogenophilales, Methylophilales, Neisseriales (e.g., the family Neisseriaceae, or *Neisseria* sp.), Nitrosomonadales, Rhodocyclales, and Procabacteriales. A particular family of Burkholderiales being considered herein is Comamonadaceae. Some particular genera of Comamonadaceae being considered herein are Acidovorax, Aquabacterium, Brachymonas, Comamonas, Curvibacter, Delftia, Hydrogenophaga, Ideonella, Leptotlrix, Malikia, Pelomonas, Polaromonas, Rhodoferax, Roseateles, Sphaerotilus, Tepidimonas, Thiomonas, and Variovorax. A particular family of Rhodocyclales being considered herein is Rhodocyclaceae. A particular genus of Rhodocyclaceae being considered herein is Azospira.

Another particular class of Proteobacteria being considered herein is Gamma Proteobacteria. Some particular orders of Gamma Proteobacteria being considered herein are Acidithiobacillales, Aeromonadales, Alteromonadales, Cardiobacteriales, Chromatiales (purple sulfur bacteria), Enterobacteriales (e.g., the family Enterobacteriaceae, such as the genera Escherichia or Salmonella), Legionellales (e.g., the family Legionellaceae, or *Legionella* sp.), Methylococcales, Oceanospirillales, Pasteurellales (e.g., the family Pasteurellaceae, or *Haemophilus* sp.), Pseudomonadales, Thiotrichales (e.g., Thiomargarita), Vibrionales (e.g., the family Vibrionaceae, or *Vibro* sp.), Xanthomonadales (e.g., the family Xanthomonadaceae, or *Xanthomonas* sp.). A particular family of Aeromonadales being considered herein is Pseudomonadaceae. A particular genus of Pseudomonadaceae being considered herein is Pseudomonas (e.g., *P. aeruginosa*). Some particular families of Alteromonadales being considered herein are Shewanellaceae and Pseudoalteromonas. A particular genus of Shewanellaceae being considered herein is Shewanella (e.g., *S. putrefaciens*).

Another particular class of Proteobacteria being considered herein is Delta Proteobacteria. Some particular orders of Delta Proteobacteria being considered herein are Aeromonadales, Bdellovibrionales (e.g., the family Bdellovibrionaceae, or *Bfdellovibrio* sp.), Desulfobacterales, Desulfovibrionales, Desulfurellales, Desulfarcales, Desulfuromonadales, Myxococcales (Myxobacteria), and Syntrophobacterales. A particular family of Aeromonadales being considered herein is Aeromonadaceae. A particular genus of Aeromonadaceae being considered herein is Aeromonas. Some particular families of Desulfuromonadales being considered herein are Desulfuromonadaceae, Pelobacteraceac, and Geobacteraceae. A particular genus of Desulfiromonadaceae being considered herein is Desulfiromonas. A particular genus of Geobacteraceae being considered herein is Geobacter (e.g., *Geobacter sufurreducens* and *Geobacter metallireducens*). A particular family of Desulfobacterales being considered herein is Desulfobulbaceae. A particular genus of Desulfobulbaceae being considered herein is Desulfobulbus.

Another particular class of Proteobacteria being considered herein is Epsilon Proteobacteria. Some particular orders of Epsilon Proteobacteria being considered herein are Campylobacterales (e.g., the family Helicobacteraceae, or *Helicobacter* sp.) and Nautiliales.

In another particular embodiment, the microbes include one or more bacteria from the phlyum Acidobacteria. A particular order of Acidobacteria being considered herein is Acidobacteriales. A particular family of Acidobacteriales being considered herein is Acidobacteriaceae. Some particular genera of Acidobacteriaceae being considered herein are Acidobacterium, Geothrix, Holophaga, and Chloracidobacterium.

In another particular embodiment, the microbes include one or more thermophilic bacteria from the order Thermotogales. Some particular genera of Thermotogales being considered herein are Thermotoga, Caldotoga, Fervidobacterium, Geotoga, Marinitoga, Petrotoga, Thermopallium, and Thermosipho. A related family of thermophilic bacteria being considered herein is Thermoanaerobiaceae. Some particular genera of Thermoanaerobiaceae being considered herein are Thennoanaerobacter and Thermoanaerobacterium. Some particular species of Thermoanaerobacter being considered herein are *Thermoanaerobacter thermohydrosulfuricus, Thermoanaerobacter subterraneus, Thermoanaerobacter brockii, Thermoanaerobacter yonseiensis,* and *Thermoanaerobacter tengcongensis.*

In another embodiment, the microorganisms considered herein are archaea. Some examples of phyla of archaea considered herein are the Crenarchaeota, Euryarchaeota, Korarchaeota, and Nanoarchaeota. Several classes of archaea are methanogens, e.g., Methanomicrobia, Methanobacteria, Methanococci, and Methanopyri. Preferably, methanogens are not used in the method due to their propensity for producing methane and their general lack of ability to function as exoelectrogenic organisms. However, methanogens that can function as exoelectrogenic organisms may be used in the method if they are used under conditions that prevent methane production.

The microbes used in the MFC can be selective or non-selective with respect to oxidative degradation of inhibitor compounds. For example, a consortium or species of microbes may be used which is generally non-selective in its ability to oxidatively degrade one or more inhibitor compounds, i.e., the microbes can oxidatively degrade a wide number of different inhibitor compounds. A consortium or species of microbes may also be somewhat selective in processing inhibitor compounds in that the microbes may oxidatively degrade one or more types of inhibitor compounds more efficiently or effectively than one or more other types of inhibitor compounds. Finally, a consortium or species of microbes may be highly selective in processing one or more specific inhibitor compounds while being essentially inefficient or ineffective in processing one or more other inhibitor compounds.

In one embodiment, a population of microbes incorporated into the MFC is relatively homogeneous by having a predominant proportion of the microbe population (typically at least 90%, 95%, 97%, 98%, or 99%) within a particular class, order, family, genus, or species of microorganism. In another embodiment, a population of microbes incorporated into the MFC is relatively heterogeneous (i.e., a consortium of microbes). A relatively homogeneous or heterogeneous sample of microbes can be obtained by any method known in the art, including as a purified culture (i.e., as prepared by cell culturing methods) or from a non-cultured source. Some examples of non-cultured sources from which a population of microbes can be obtained for the MFC include, for example, a waste stream (e.g., municipal or industrial waste streams), top soil, hot spring, estuary, deep sea vent, underground, or chemically contaminated environment.

In one embodiment, a single MFC is capable of oxidatively degrading a wide number of inhibitor compounds, thereby enabling the MFC to remove the majority (or all) of the different types of inhibitor compounds that may be present in the process water. The single MFC may also be a single system of MFCs, all having the same ability to degrade the same types of inhibitor compounds. In another embodiment, a multiplicity of MFCs (i.e., two or more), each containing microbes that are specialized for degrading specific inhibitor compounds, are used in the process to remove the majority (or all) of the different types of inhibitor compounds that may be present in the process water.

Examples have been set forth below for the purpose of illustration and to describe certain specific embodiments of the invention. However, the scope of this invention is not to be in any way limited by the examples set forth herein.

EXAMPLE 1

MFC Construction

The MFC used in this study has a two-chamber design (FIG. 1). The microbial enrichment was carried out using an air-cathode, consisting of a platinum-deposited carbon electrode. The anode chamber (4 cm diameter×1.27 cm thickness) contained a carbon felt electrode separated from the cathode by a Nafion-115 membrane. The anode chamber was a compact, flow-through system with high electrode surface area to volume ratio (45,230 $m^2/m^3$). The projected surface area of the anode was 12.57 $cm^2$ and was used to calculate power density. A gold wire was used as a current collector for the air-cathode and a graphite rod was used for the anode. A ferricyanide cathode was used for determining the maximum power density.

EXAMPLE 2

Inoculation and Operation

The anode chamber of the MFC (MFC-A) was inoculated with a 10 mL culture sample from an MFC enriched with acetate as the energy source. The inoculum was added directly into the flow line entering the anode chamber, and carried into the anode chamber by the deaerated recirculating medium.

The nutrient medium (Medium AC-1) used for enrichment consisted of 975 mL of a sterile mineral solution and 12.5 mL, each of filter sterilized Wolfe's mineral solution and vitamin solution (Gorby, Y. A., et al., *PNAS*, 103, 11358-11363 (2006)). The mineral solution was made up of 0.31 g $NH_4Cl$, 0.13 g KCl, 4.97 g $NaH_2PO_4.H_2O$, and 2.75 g $Na_2HPO_4.H_2O$ per liter of nanopure water (see, for example, Liu, H. et al., *Environ. Sci. Technol.*, 38, 4040-4046 (2004)), which was adjusted to a pH of 7.0 with 1N NaOH prior to sterilization. The nutrient medium AC-1 (200 ml) was placed in a glass bottle reservoir (anode liquid reservoir) and recirculated through the anode chamber at 4-7 mL/min (FIG. 1A). The medium was deaerated with nitrogen to remove the dissolved oxygen.

The nutrient medium was placed in a glass bottle reservoir (anode liquid reservoir, 200 mL)) and recirculated through the anode chamber at 4-7 mL/min. The medium was deaerated with nitrogen. The enrichment process included replacement of the recirculating medium intermittently (whenever optical density at 600 nm increased above 0.05) to eliminate planktonic bacteria and mediators and enrich exoelectrogenic biofilm-forming organisms.

The carbon source added to the anode liquid reservoir was a mixture of fermentation inhibitors which included 0.2 g/L 2-furfural, 0.1 g/L 4-hydroxybenzaldehyde (HB), 0.1 g/L 4-hydroxyacetophenone (HAP) and 0.5 g/L vanillic acid (VA). Acetate was also added for the first seven days, but in a continuous manner using a syringe pump at the rate of 0.2 g/L-day. All other substrates were added all at once, at time zero, and tracked until complete disappearance was observed. The anode medium was modified with 0.4 g/L glucose on day 7 primarily to enhance the microbial growth. The initial external resistance (load) applied to the MFC was 500 Ohms (500Ω), which was reduced to 100Ω when the voltage output increased above 0.2 volts (day 10), and then reduced to 50Ω (day 12). The MFC was tested with individual inhibitors from day 20 to day 45 by adding them at 0.05-0.2 g/L concentration. The conversion of 5-hydroxymethylfurfural (HMF) was also investigated. A second experiment was conducted with acetate using a different MEC (MFC-B) to examine the conversion of acetate. Conversion of acetate to electricity was studied at 0.1 g/L and 0.3 g/L concentrations. The acetate was added in a fed-batch manner and the voltage output was measured until all the acetate was removed.

Figure 2A:
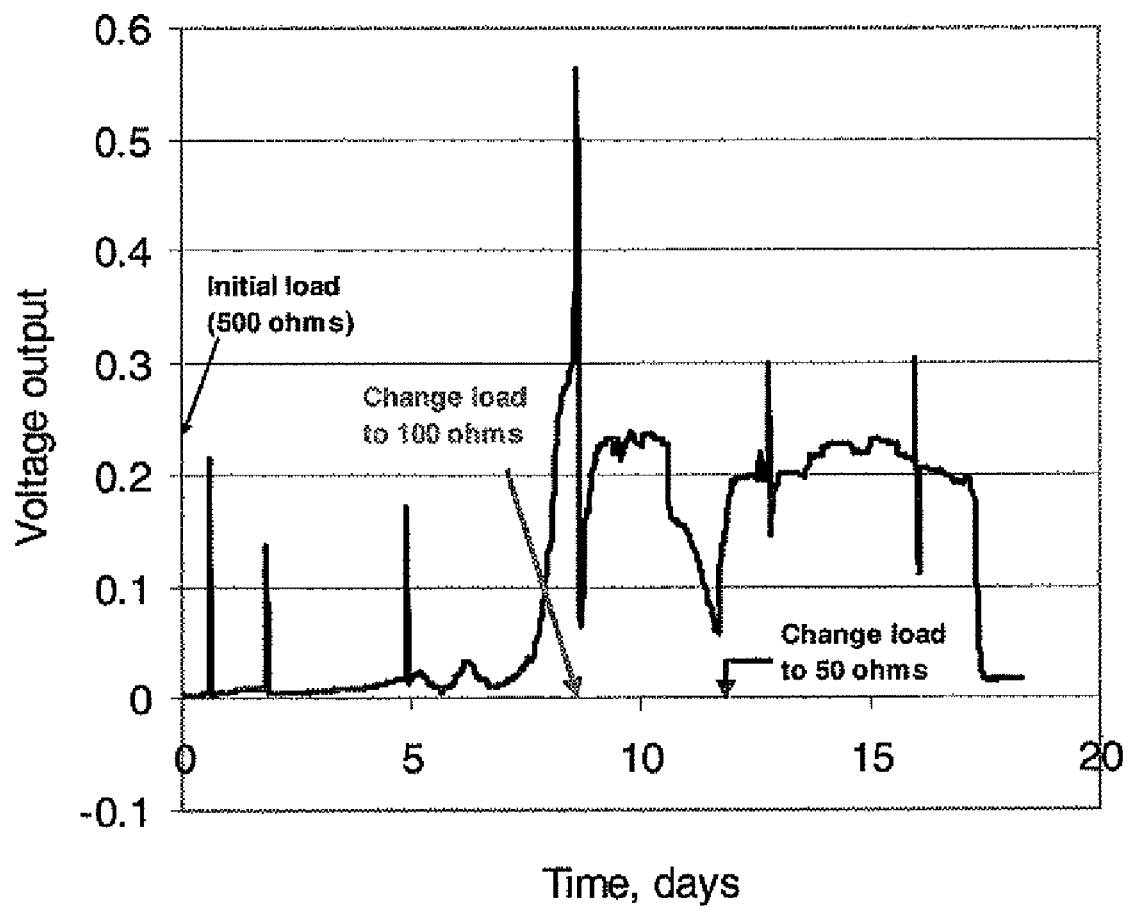
FIG. 2A. Graph showing voltage output during growth of an inhibitor-consuming microbial consortium in a microbial fuel cell (MFC-A). Inhibitors being fed to the microbes include furfural, vanillic acid, 4-HAP, and 4-HB.
Figure 2B:
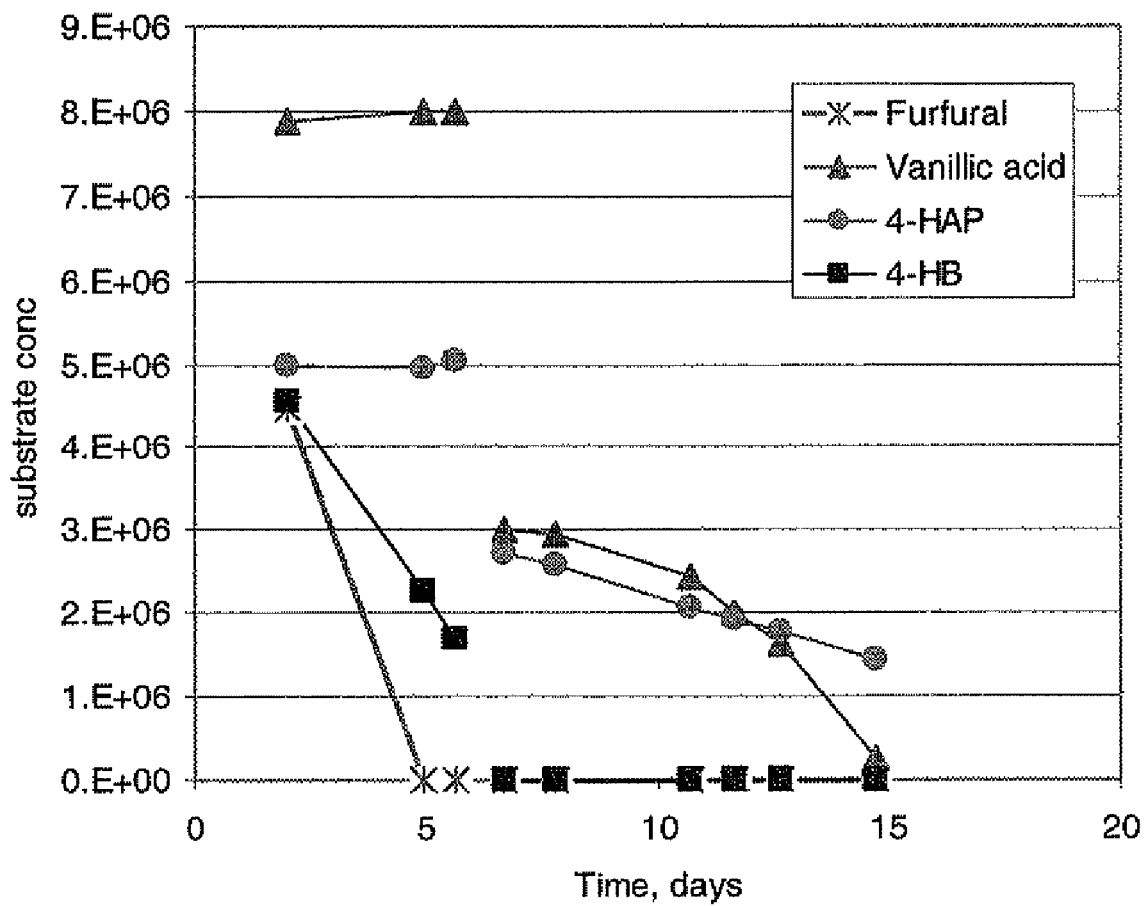
FIG. 2B. Graph showing time for the removal of furfural, vanillic acid, 4-HAP, and 4-HB inhibitors by an inhibitor-consuming microbial consortium in a microbial fuel cell (MFC-A).
Figure 2C:
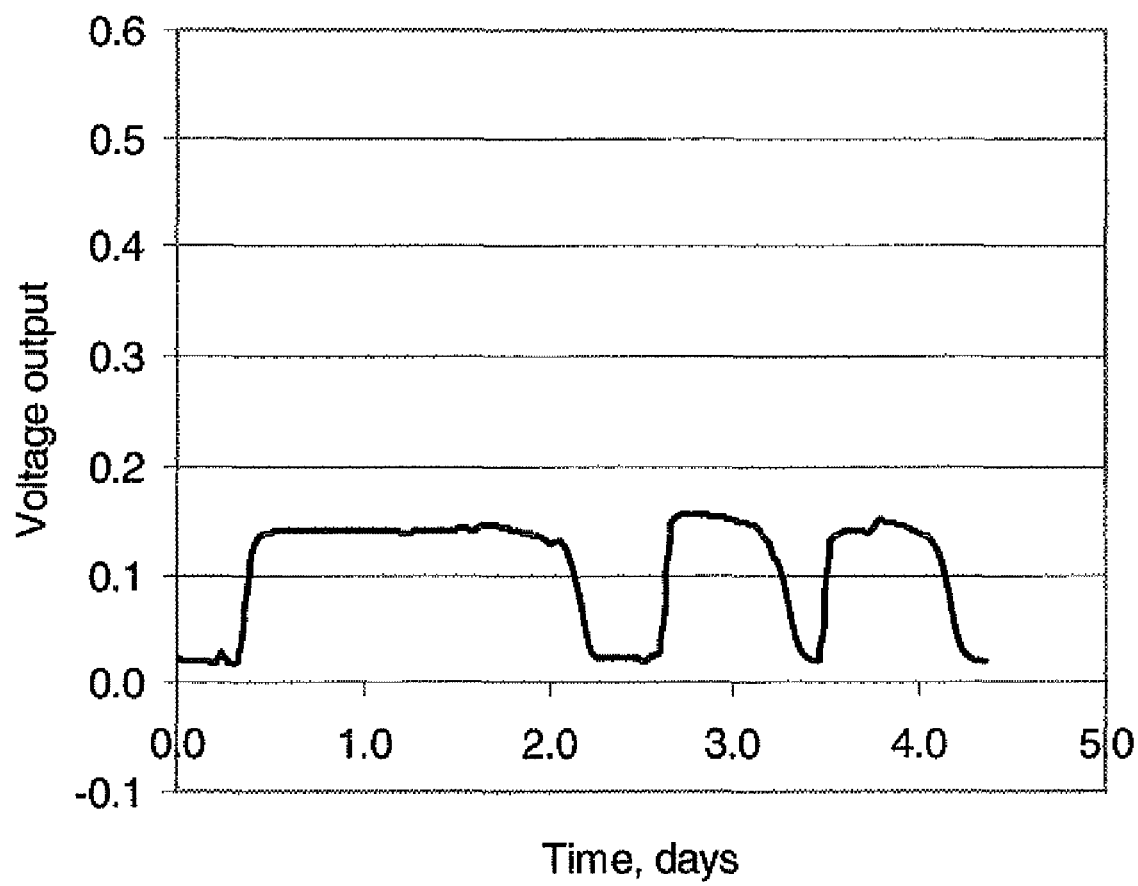
FIG. 2C. Graph showing voltage output during growth of an inhibitor-consuming microbial consortium in a microbial fuel cell (MFC-B). Inhibitor being fed to the microbes is acetate.
Figure 2D:
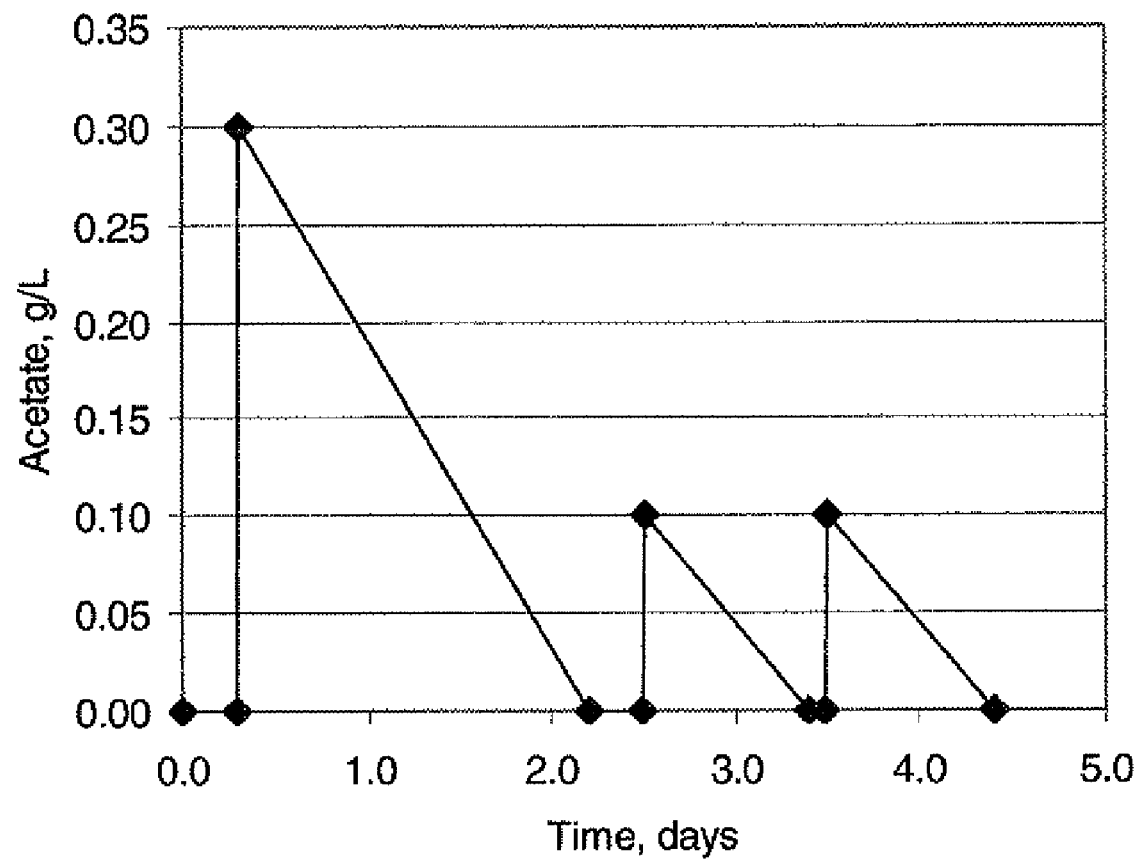
FIG. 2D. Graph showing time for the removal of acetate by an inhibitor-consuming microbial consortium in a microbial fuel cell (MFC-B).

Increase in voltage output from the MFC (FIG. 2A) indicated growth of the microbial consortium in the anode chamber. While the voltage output was low for the first 7 days, the trend correlated well with consumption of two of the substrates, HB (day 5) and 2-furfural (day 7). The concentration of the inhibitors remaining after day 7 was reduced by dilution with fresh medium at a ratio of 1:3 to minimize potential inhibitory effects of the phenolic compounds and promote microbial growth. A particular order of depletion was observed for the substrates added. As indicated, HB was the first one to be consumed, followed by 2-furfural, VA and HAP, in that order (FIG. 2B). Glucose was consumed immediately after it was added on day 7, with a concomitant rise in voltage output from 0.02 V to 0.3 V (days 7-8) as shown in FIG. 2A. The conversion of acetate using a consortium enriched on acetate is shown in FIG. 2C. FIG. 2D demonstrates that the amount of electricity produced was proportional to the amount of acetate added.

EXAMPLE 3

Effect of Inhibitor Concentration on the Microbial Consortium

After confirmation of electricity production from individual inhibitor molecules, the effect of inhibitor concentration on their removal and electricity production was studied. The experiments were conducted by adding each of the substrates individually, at the various concentrations to study substrate inhibition. From day 51 to 62, HB was used as the energy source for the MFC at concentrations from 0.1 to 1 g/L. From day 63 to day 82, 2-furfural was used as the energy source at a concentration from 0.05 to 2 g/L. From day 83 to day 101, VA was used as the substrate from 0.05 to 4 g/L, followed by use of HMF as substrate from day 129 to day 150 at a concentration from 0.2 to 2 g/L. The MFC was operated with 2-furfural as the substrate between day 102 to 128. Effect of acetate was studied in MFC-B up to a concentration of 10 g/L. The voltage output was monitored at each concentration for a period of up to five days.

Figure 3:
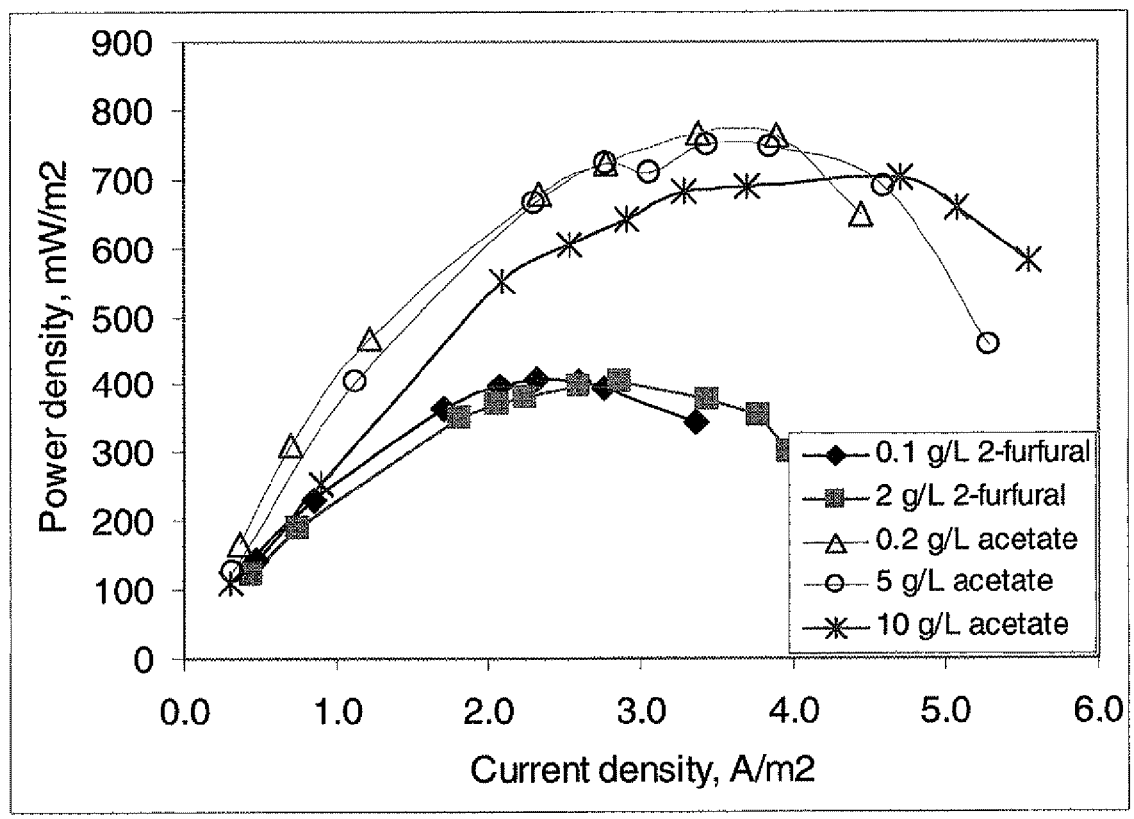
FIG. 3. Graph showing power density vs. current density (i.e., power density curves) for the MFC-facilitated removal of 2-furfural and acetate from an aqueous stream with concentrations up to 2 g/L and 10 g/L for each inhibitor, respectively.

The effect of 2-furfural on electricity production was studied at a concentration from 0.1 g/L to 2 g/L (20.8 mM) using an air-cathode MFC. No inhibition was observed at any concentration, as far as electricity production was concerned. It should be noted that the substrate utilization was limited by the cathode side in an air-cathode MFC used in this study. Thus, as the concentration was increased, the voltage output did not increase, but the period for which electricity is produced increased proportionately with the amount of substrate added. Similar results were obtained for HMF (0.1 to 2 g/L), HB (0.1 g/L to 1 g/L) and VA (0.1 to 4 g/L). The effect of acetate concentration was also studied in a different MFC (MFC-B) using a consortium enriched on acetate. The power densities obtained using acetate and 2-furfural as substrates in an air-cathode MFC are shown in FIG. 3.

EXAMPLE 4

Power Density Analysis

The power density analysis for the MFCs was conducted by adding the carbon source (inhibitor) to the anode liquid reservoir. The nutrient medium was completely replaced prior to every analysis, followed by fed-batch addition of the substrate into the medium (at 0.2 g/L). Two different cathodes were used for the power density analysis: the air-cathode and a ferricyanide-cathode. A 200 mM potassium ferricyanide in 100 mM potassium phosphate buffer was used as the catholyte for the latter. The analysis was conducted 60 minutes after addition of the carbon source to allow the voltage output to stabilize. A variable resistor ranging from 0-5000 ohms was used. Voltage was recorded by a Fluke multimeter Model 83. The resistance sweep was conducted at an interval of 5 minutes. The maximum power density was confirmed by operating the MFC at the particular resistance for at least one hour following the power density analysis. Multiple measurements of the voltage output at the resistance exhibiting maximum power density were made on different days to determine reproducibility of the power density curve. The results were found to be within a 10% standard deviation.

Figure 4:
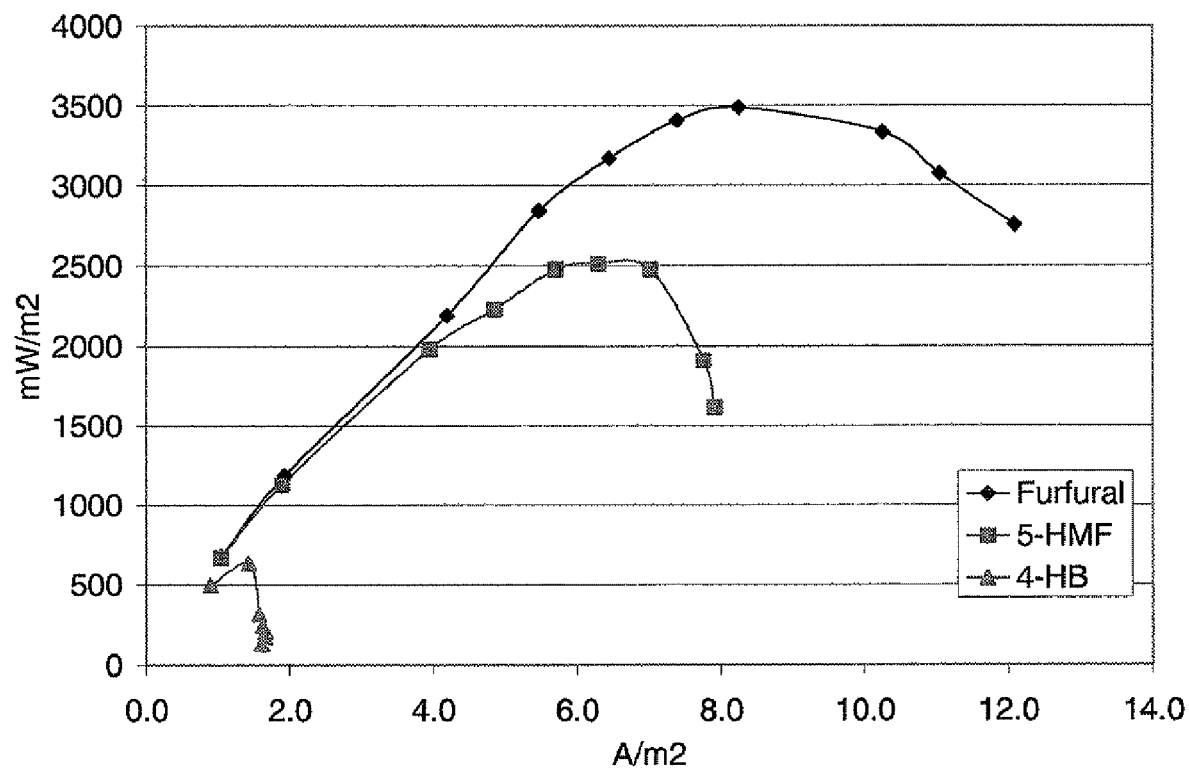
FIG. 4. Graph showing power density vs. current density (i.e., power density curves) for the MFC-facilitated removal of furfural, 5-HMF, and 4-HB at a concentration of 0.2 g/L, using a ferricyanide cathode.

The use of ferricyanide-based cathode has been shown to result in higher power densities as compared to Pt-based air-cathodes (see, for example, Oh S., et al., "Cathode performance as a factor in electricity generation in microbial fuel cells" in *Environ. Sci. Technol* 2004, 38(18): 4900-4904). Ferricyanide was therefore used to determine the maximum power density. Each of the inhibitors were studied individually with the ferricyanide cathode. The results for 2-furfural, 5-HMF and HB are shown in FIG. 4. A maximum power density of 3490 mW/m$^2$ (332 W/m$^3$) was obtained with 2-furfural as the substrate. HMF produced 2510 mW/m$^2$ (238 W/m$^3$), while HB produced 630 mW/m$^2$ (59 W/m$^3$). In the foregoing cases, an anode specific surface area of 79 m$^2$/m$^3$ and an NAV value of 0.83 was used for converting the area power density (units of W/cm$^2$) to volumetric power density (units of W/cm$^3$). The electricity produced with VA and HAP as substrates was 150 mW/m$^2$ and 9 mW/m$^2$, respectively (data not shown). It was observed that the power output from the MFC using the individual phenolic substrates was dependent on the time the MFC was operated with the particular substrate. This indicated that the microbial population had not yet been optimally enriched with microbes capable of consuming a particular substrate. The low power density for these substrates was probably due to the low initial population of the organisms capable of using these substrates.

The coulombic efficiency (CE) for furfural, HB, and HMF were determined to be 69 ±3%, 64±4% and 60±4%, respectively. HPLC analysis of the samples during the course of the run indicated a few intermediates (currently not characterized) which were eventually consumed. The CE for conversion of VA and HAP was not quantified due to low voltage output from these two substrates. HPLC analysis of samples collected from the MFC anode solution containing VA showed production of several intermediates. These appeared at 23.7, 22.3 and 16 minutes, as compared to 25.4 minutes for VA. These intermediates were also consumed by the MFC consortium without significant electricity production.

The amount of electricity produced from the bioconversion of the inhibitor molecules depends on the degree of mineralization of the molecules. Incomplete conversion leads to low coulombic efficiency and byproducts. The coulombic efficiency and HPLC data indicate near complete mineralization of the 2-furfural and HMF, although this was not the case for the lignin-degradation model compounds.

EXAMPLE 5

Genetic Characterization 16S clone library. Microbial samples were collected from the anode of MFC on day 83 by dislodging the cells from the electrode using a hypodermic needle, followed by withdrawal of the cells using a syringe from the exit of the MFC anode. Genomic DNA was isolated using the standard freeze-thaw procedure, followed by phenol-chloroform extraction (P. L. Bond, et al., *Applied and Environmental Microbiology*, 66, 3842-3849 (2000)). Multiple sequences were initially aligned against the most similar sequences in the Ribosomal Database Project II (RDP II) and assigned to a set of hierarchical taxa using a Naïve Bayesian rRNA classifier version 1.0.

Orientation of the sequences was checked using program OrientationChecker v.1.0. Sequences with unknown orientation were omitted from further analyses. Clone libraries were checked for the presence of chimeric sequences using the program Bellerophon (see Huber T., et al., "Bellerophon: a program to detect chimeric sequences in multiple sequence alignments" *Bioinformatics,* 2004, 20:2317-2319) and the Chimera Detection program in the RDP II. Putative chimeras were excluded from further analyses. Closest relatives were retrieved from NCBI GeneBank following BLAST search (see Altschul S. F., et al., "Basic local alignment search tool" *J. Mol. Biol.,* 1990, 215:403-410). To determine the clone library coverage for each sample, statistical analyses were performed using DOTUR (see Schloss P. D., et al., "Introducing DOTUR, a computer program for defining operational taxonomic units and estimating species richness" *Appl. & Environ. Microbiol.,* 2005, 71:1501-1506). The population distribution is reported as a percentage of the total number of bacterial clones sequenced for each sample.

Figure 5:
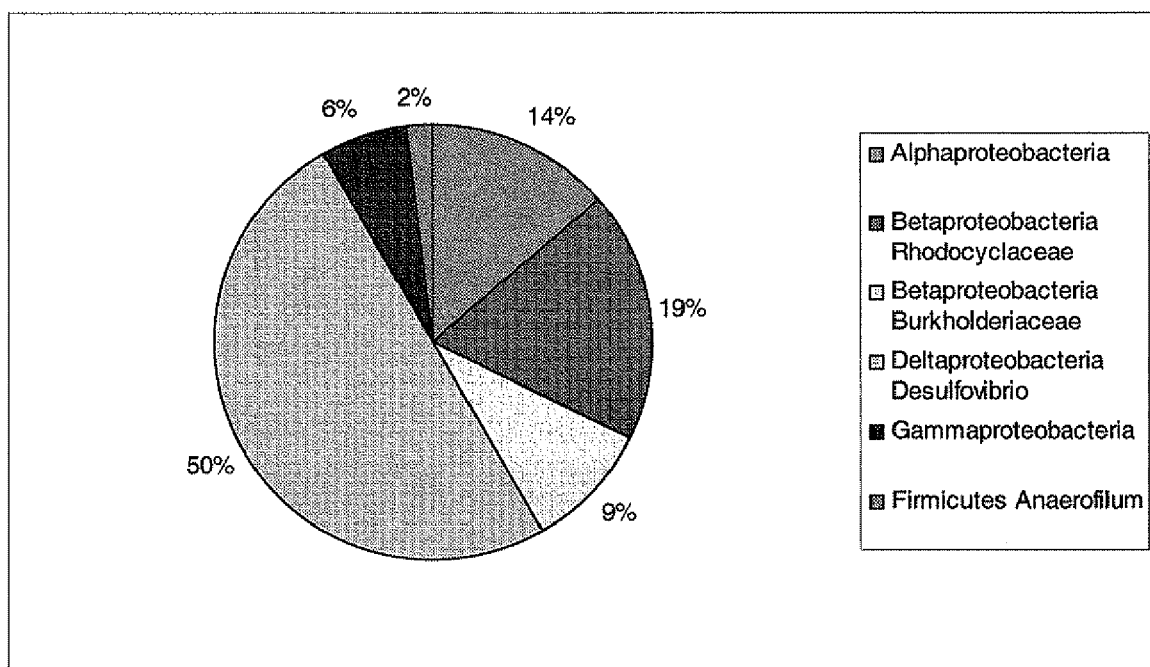
FIG. 5. Pie graph showing the distribution of the microbial population in an MFC enriched on inhibitor compounds.

A total of 95 clones were sequenced from a library created from the sample collected on day 63 from the MFC anode. The microbial sample was dominated by an organism which constituted 47% of the clone library population (45 clones from a total of 95 clones sequenced) (FIG. 5). The closest match to this group was a Proteobacterium, Core-3 strain enriched in a consortium in an electrochemically-assisted bioreactor using iron for respiration. The 45 strains were not all similar and exhibited between 92-99% similarity to the strain Core-3. Additionally, the closest known genus similar to this group of organisms was *Desulfovibrio* (92-99% similarity). This group was designated as Group A (Table 1). The similarity data given here is based on 16S rRNA obtained using BLAST or PLAN.

Figure 6:
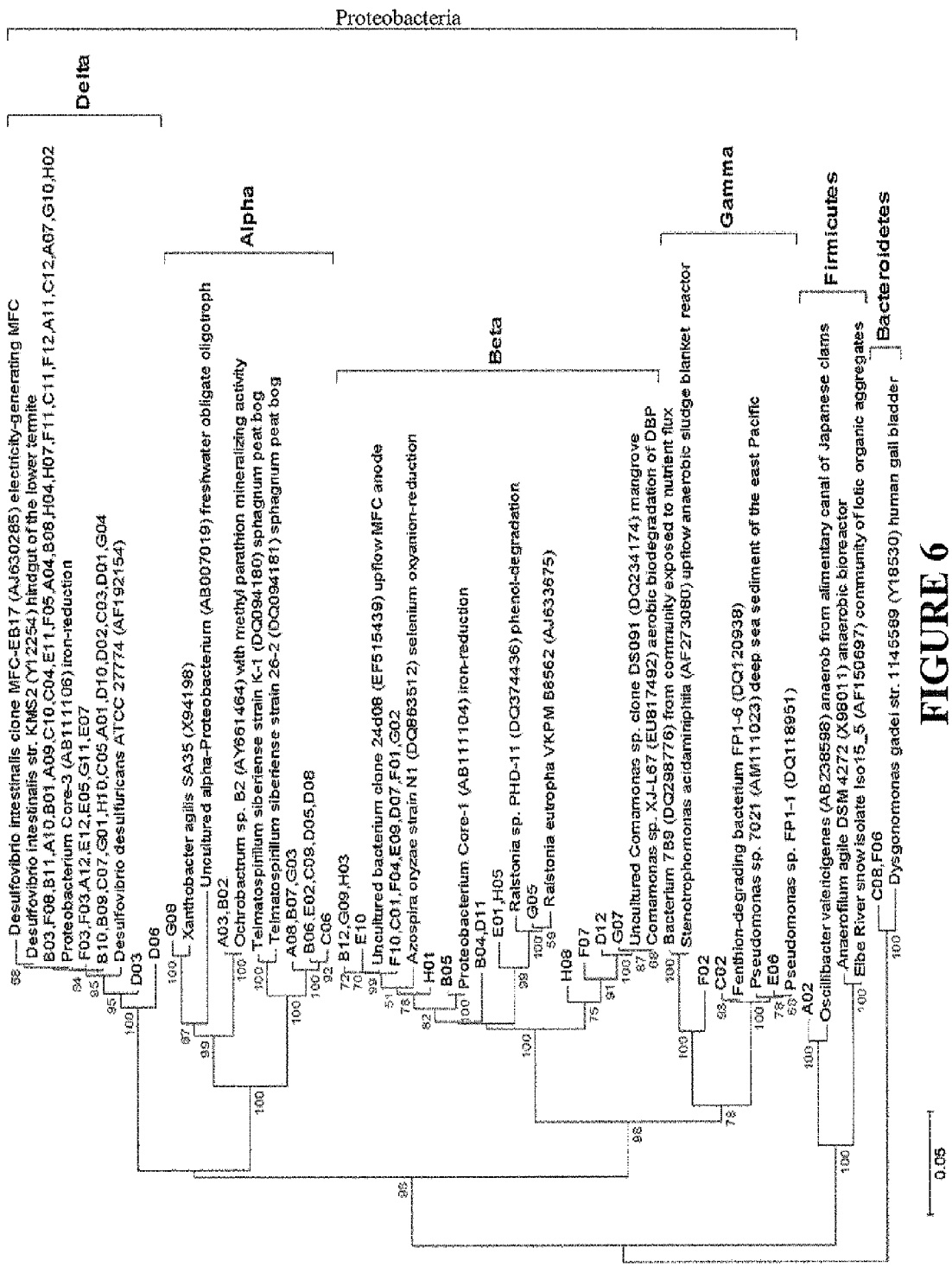
FIG. 6. Phylogenetic tree of an MFC consortium enriched on inhibitor compounds.

The remaining 53 clones in the library had significant diversity representing more than 19 genera. Of these 53 clones, 25 clones were similar to potential exoelectrogens reported in literature. These 25 clones were divided into four groups (B-E, see Table 1). The group B (12 clones) showed between 94-99% similarity to a strain 24dO8 enriched from an MFC by Angenent's group (EF515439). This group was similar to the genus *Azospira* (89-97% similarity). The Group C (3 clones) exhibited 95% similarity to a Proteobacterium Core-1, which came from the same electrochemical bioreactor as Core-3. The Group D (9 clones) exhibited 94-97% similarity to an organism, Proteobacterium LS-1, which was also from the same electrochemical bioreactor as Core-3. The Group E (1 clone) was similar to an α-Proteobacteria strain MFC4-10 (A# AB286268) enriched on cellulose as the carbon source. The phylogenetic tree for the MFC community is shown in FIG. 6. As shown, 69% of the population showed some level of similarity to potential exoelectrogens reported in the literature. The details of the percent similarity and query coverage for all clones is given in Table 1 below.

TABLE 1

Distribution of microbial population in MFC

| Clone # | Closest known genus | Accession # | Query Coverage, %[1] | % similarity | Group No.[2] |
|---|---|---|---|---|---|
| D04, D09 | *Anaerofilum agile* | X98011.1 | 97 | 89 | |
| A01, A04, A05, A06, A07, A09, A10, A11, A12, B01, B03, B08, B09, B10, B11, C03, C04, C05, C07, C10, C11, C12, D01, D02, D03, D06, D10, E03, E05, E07, E11, E12, F03, F05, F08, F11, F12, G01, G04, G10, G11, H02, H04, H07, H10 | *Desulfovibrio intestinalis,* strain KMS2 | Y12254.1 | 98 | 92-99 | A |
| B04, B05, D11 | *Azospira oryzae* strain N1 | DQ863512.1 | 100 | 94-95 | B |
| B12, C01, D07, E09, F01, F04, F10, G02, G09, H01, H03, H11, G12, E10 | *Azospira oryzae* strain N1 | DQ863512.1 | 100 | 89-97 | C |
| G06 | *Azospira oryzae* strain N1 | DQ863512.1 | 100 | 89 | |
| C08, F06 | *Dysgonomonas gadei* strain 1145589 | Y18530.1 | 98 | 95 | |
| F07, C02, H09 | Fenthion-degrading bacterium FP1-6 | DQ120938.1 | 100 | 91-98 | |
| A02 | *Oscillibacter valericigenes* sp. | AB238598.1 | 97 | 95 | |
| H06, H08 | *Pseudomonas testosteroni* sp. | M11224.1 | 96-100 | 90-96 | |

TABLE 1-continued

Distribution of microbial population in MFC

| Clone # | Closest known genus | Accession # | Query Coverage, %[1] | % similarity | Group No.[2] |
|---|---|---|---|---|---|
| H05, E01 | *Ralstonia eutropha* H16 | AM260479.1 | 100 | 92 | |
| A08, B07, G03 | *Telmatospirillum siberiense* strain 26-2 | DQ094181.1 | 92 | 95 | D-1 |
| B06, C06, C09, D05, D08, E02 | *Telmatospirillum siberiense* strain K-1 | DQ094180.1 | 92 | 95 | D-2 |
| E04 | *Ralstonia metallidurans* CH34 | CP000353.1 | 100 | 87 | E |
| G05 | *Ralstonia metallidurans* CH34 | CP000353.1 | 100 | 98 | |
| G07 | *Comamonas* sp. XJ-L67 | EU817492.1 | 99 | 99 | |
| A03, B02 | *Ochrobactrum* sp. 1605 | DQ989292.1 | 100 | 99 | |
| E06 | *Pseudomonas* sp. FP1-1 | DQ118951.1 | 99 | 99 | |
| D12 | *Pseudomonas testosteroni* | M11224.1 | 100 | 99 | |
| E08, G08 | *Ralstonia* sp. PHD-11 | DQ374436.1 | 100 | 90 | |
| F02, F09 | Bacterium 7B9 | DQ298776.1 | 94-100 | 90-94 | |

[1]The query coverage and percent similarity are based on a 16S rRNA homology search conducted using nucleotide BLAST.
[2]The group no. is provided only for clones which were similar to potential exoelectrogens.

The other clones demonstrated similarity to organisms capable of degradation of various xenobiotic molecules including phenols, methyl parathion, and fenthion, as well as those capable of selenium reduction. Some of these organisms may also be exoelectrogenic; however, the closest organism to these clones based on similarity analysis using BLAST was not a known exoelectrogen.

None of the 95 clones sequenced showed 100% similarity to any known organisms. Three of the 95 clones showed 99% similarity to known isolated organisms of which one was a *Comamonas* sp. and the other two, *Pseudomonas* sp.

The potential exoelectrogens identified in the MFC-A demonstrated 89-99% similarity to reported exoelectrogens. Although about 74% of the clones sequenced from the 16S clone library of the MFC sample showed similarity to known exoelectrogens, very little is known about how the organisms may be interacting with electrode materials. The phylogenetic tree demonstrates the significant microbial diversity of these organisms and indicates that such organisms may be present in diverse environments such as termite gut, anaerobic sludge reactors, sediments, metal-reducing environments, insecticide-contaminated environments, and other sources.

EXAMPLE 6

Biorefinery Process

Figure 7:
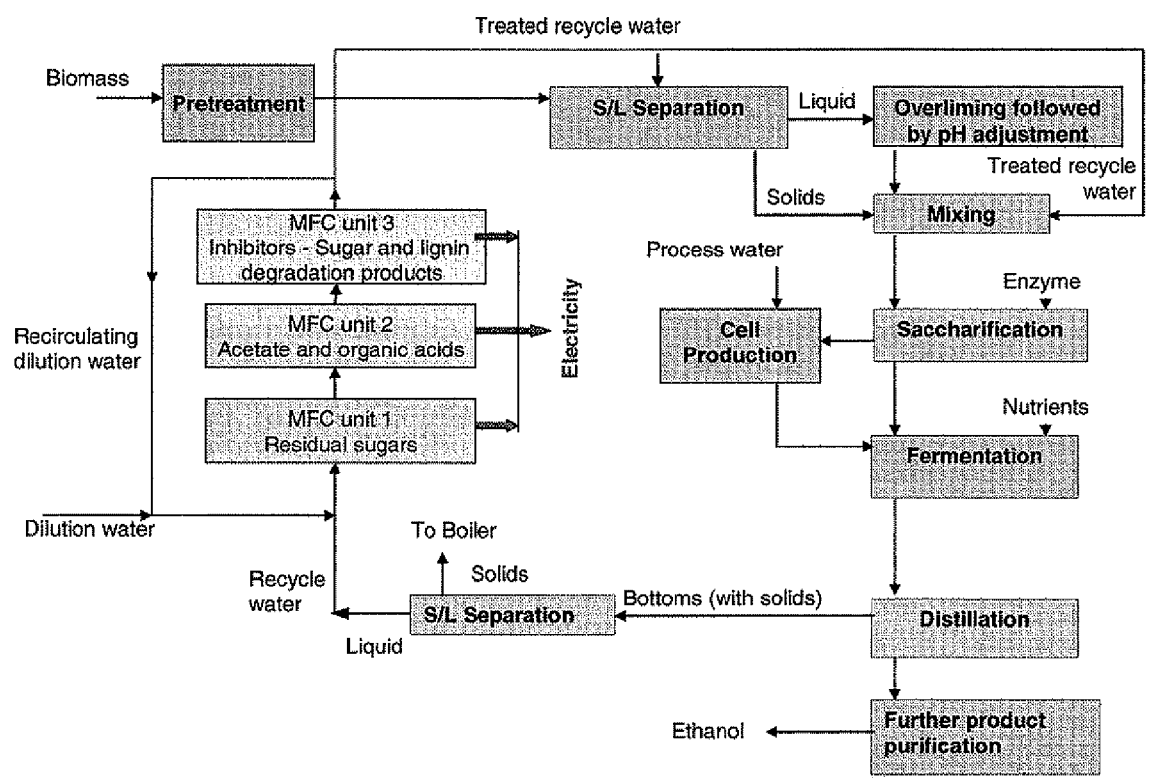
FIG. 7. A biorefinery flow sheet showing the location of MFC units capable of removing inhibitor compounds from a recycled process stream.

Removal of fermentation inhibitors in a cellulosic ethanol process was demonstrated. FIG. 7 is a process schematic (flow sheet) showing points of application of MFCs in a typical cellulosic ethanol process employing dilute acid pretreatment of corn stover. The use of MFCs in the recycle stream coming from the distillation tower reduces accumulation of the inhibitors and enables recycling of the process water Table 2 below shows the ethanol yield and acetate levels for different process conditions (Schell, *DOE OBP Biochemical Processing Integration, Biochemical Platform Review Meeting*, Denver, Colo., Aug. 7-9, 2007). Besides acetate, other inhibitors present in the hydrolyzate may significantly affect the ethanol yield. However, the concentration of acetate can be representative of the level of total inhibitors in the hydrolyzate, and thus, can provide a qualitative assessment of the effect of inhibitors. Table 2 shows that if the concentration of acetate is reduced below 10 g/L, ethanol yields above 65% can be attained.

TABLE 2

Effect of solids loading and water recycle on ethanol yield

| % solids loading, % water recycle | Ethanol yield (%) | Acetate concentration in hydrolyzate (g/L) |
|---|---|---|
| 10% solids, 10% recycle | 79 | 7.5 |
| 10% solids, 25% recycle | 73 | 12 |
| 25% solids, 10% recycle | 65 | 10 |
| 25% solids, 25% recycle | 5 | 13 |

The ability of MFCs to reduce levels of acetate and other inhibitors in the recycle stream, preferably below 0.1 g/L, prevents the precipitous drop in ethanol yields. For solids loading above 25%, the increase in ethanol yields from 5% (at 13 g/L acetate) to 79% (at 7.5 g/L acetate) improves the economic feasibility of the cellulosic ethanol process. The savings resulting from water recycle and the produced electricity further improves the economic feasibility of the process.

While there have been shown and described what are at present considered the preferred embodiments of the invention, those skilled in the art may make various changes and modifications which remain within the scope of the invention defined by the appended claims.

What is claimed is:

1. A method for removing inhibitor compounds from a cellulosic biomass-to-ethanol process which includes a pretreatment step of raw cellulosic biomass material and the production of fermentation process water after production and removal of ethanol from a fermentation step, the method comprising contacting said fermentation process water with an anode of a microbial fuel cell, said anode containing microbes thereon which oxidatively degrade one or more of said inhibitor compounds while producing electrical energy from said oxidative degradation, and wherein said anode is in electrical communication with a cathode, and a porous material separates said anode and cathode.

2. The method of claim 1, wherein said microbes are substantially in the form of a biofilm on said anode.

3. The method of claim 1, wherein said pretreatment step includes reaction with an acid.

4. The method of claim 1, wherein said pretreatment step includes a hot water solvolysis, wet oxidation, steam explosion, alkali treatment, ammonia treatment, or elevated temperature step.

5. The method of claim 1, wherein at least a portion of fermentation process water that has been cleansed of inhibitors is continuously recycled into the cellulosic biomass-to-ethanol process.

6. The method of claim 5, wherein at least 25% of the water is continuously recycled.

7. The method of claim 1, wherein the process is operated such that residual levels of sugars, oligosaccharides, polysaccharides, sugar degradation products, ethanol, lignin degradation products and/or lignin are present in the fermentation process water, wherein these materials are consumed by the microbes of the microbial fuel cell such that additional electrical energy is produced therefrom.

8. The method of claim 1, wherein the process is operated such that the loading rate of inhibitors and any other consumables in the fermentation process water entering the microbial fuel cell is at or below a loading rate at which the microbial fuel cell can operate at a maximum electrical output capacity and coulombic efficiency.

9. The method of claim 8, wherein the loading rate is 90% or less of a loading rate at which the microbial fuel cell can operate at a maximum electrical output capacity.

10. The method of claim 8, wherein the loading rate is 80% or less of a loading rate at which the microbial fuel cell can operate at a maximum electrical output capacity.

11. The method of claim 1, wherein said anode comprises a form of elemental carbon.

12. The method of claim 1, wherein the cathode of said microbial fuel cell is a Pt/air electrode.

13. The method of claim 1, wherein the anode is operated in the substantial absence of oxygen.

14. The method of claim 1, wherein a first microbial fuel cell generates electrical energy from the consumption of one or more non-inhibitor nutrient compounds or materials, and a second microbial fuel cell generates electrical energy from the consumption of inhibitor compounds.

15. The method of claim 1, wherein a first microbial fuel cell generates electrical energy from the consumption of one or more inhibitor compounds or materials, and a second microbial fuel cell generates electrical energy from the consumption of one or more other inhibitor compounds or materials.

16. The method of claim 1, wherein electrical power generated by the microbial fuel cell is used to power one or more processes in the cellulosic biomass-to-ethanol process.

17. The method of claim 16, wherein at least one process being electrically powered by the microbial fuel cell is selected from: heating of fermentation process water, ethanol separation from fermentation process water, and heating for removal of water from unconverted biomass.

18. The method of claim 1, wherein the cathode of said microbial fuel cell is operated in the substantial absence of oxygen.

19. The method of claim 1, wherein the microbial fuel is operated such that hydrogen gas is produced at the cathode by operating the microbial fuel cell under the condition that the cathode is constructed of a hydrogen-producing material and is deoxygenated, and the cell potential of the microbial fuel cell is adjusted by application of an external voltage such that hydrogen is produced at the cathode, with the provision that the porous material is optional.

20. The method of claim 19, wherein the hydrogen gas is used as a fuel source to power one or more processes in the cellulosic biomass-to-ethanol process.

21. The method of claim 19, wherein said hydrogen is processed in a hydrogen-oxygen fuel cell to convert the hydrogen to electricity.

22. The method of claim 20, wherein at least one process being powered by the hydrogen gas is heating of fermentation process water, ethanol separation from fermentation process water, and heating for removal of water from unconverted biomass.

23. The method of claim 1, wherein the microbial fuel cell is operated such that the cathode electrochemically reduces one or more electrochemically reducible species other than hydrogen ions.

24. The method of claim 5, wherein at least a 60% ethanol yield is maintained in the water-recycled cellulosic biomass-to-ethanol process.

25. The method of claim 5, wherein at least a 70% ethanol yield is maintained in the water-recycled cellulosic biomass-to-ethanol process.

26. The method of claim 5, wherein at least a 80% ethanol yield is maintained in the water-recycled cellulosic biomass-to-ethanol process.

27. The method of claim 1, wherein said one or more inhibitory compounds are selected from aliphatic carboxylic acids, aliphatic ketones, aliphatic aldehydes, aliphatic alcohols, aromatic carboxylic acids, aromatic ketones, aromatic aldehydes, and aromatic alcohols.

28. The method of claim 1, wherein said one or more inhibitory compounds includes acetate.

29. The method of claim 1, wherein said one or more inhibitory compounds includes furfural or a derivative thereof.

30. The method of claim 1, wherein said one or more inhibitory compounds includes one or more phenolics.

31. The method of claim 1, wherein at least 25% of process water that has been cleansed of inhibitors is continuously recycled into the cellulosic biomass-to-ethanol process while an ethanol yield of at least 60% is maintained in the cellulosic biomass-to-ethanol process.

32. The method of claim 1, wherein at least 25% of process water that has been cleansed of inhibitors is continuously recycled into the cellulosic biomass-to-ethanol process while an ethanol yield of at least 70% is maintained in the cellulosic biomass-to-ethanol process.

33. The method of claim 1, wherein a biomass loading of at least 20% is used, and at least 25% of process water that has been cleansed of inhibitors is continuously recycled into the cellulosic biomass-to-ethanol process while an ethanol yield of at least 60% is maintained in the cellulosic biomass-to-ethanol process.

34. The method of claim 1, wherein a biomass loading of at least 20% is used, and at least 25% of process water that has been cleansed of inhibitors is continuously recycled into the cellulosic biomass-to-ethanol process while an ethanol yield of at least 70% is maintained in the cellulosic biomass-to-ethanol process.

35. The method of claim 20, wherein the hydrogen is used for production of one or more chemical products.

36. The method of claim 1, wherein the cathode of said microbial fuel cell is a biocathode.

* * * * *